(12) United States Patent
Moore et al.

(10) Patent No.: US 10,356,334 B2
(45) Date of Patent: Jul. 16, 2019

(54) SYSTEMS AND METHODS FOR ILLUMINATION AND IMAGING OF A TARGET

(71) Applicant: Novadaq Technologies ULC, Burnaby (CA)

(72) Inventors: Frederick Allen Moore, Vancouver (CA); Anton Walter Lamprecht, Richmond (CA); Lesley Myron Otsig, New Westminster (CA); Paul Roald Westwick, Vancouver (CA); Muhammad Nasir al-Din bin Zulkafly, Vancouver (CA); Gavin Michael Murray, Vancouver (CA); Adam John Tynan, Vancouver (CA); James Elliott Cameron, Victoria (CA); Gregory Vincent Browne, Vancouver (CA); Isabelle Fontaine, Vancouver (CA)

(73) Assignee: NOVADAQ TECHNOLOGIES ULC, Burnaby, BC (CA)

( * ) Notice: Subject to any disclaimer, the term of this patent is extended or adjusted under 35 U.S.C. 154(b) by 83 days.

(21) Appl. No.: 15/348,664

(22) Filed: Nov. 10, 2016

(65) Prior Publication Data

US 2017/0142314 A1    May 18, 2017

Related U.S. Application Data

(60) Provisional application No. 62/255,024, filed on Nov. 13, 2015.

(51) Int. Cl.
*A61B 17/00*    (2006.01)
*A61B 46/10*    (2016.01)
(Continued)

(52) U.S. Cl.
CPC .......... *H04N 5/2354* (2013.01); *A61B 46/10* (2016.02); *A61B 90/30* (2016.02); *H04N 5/2252* (2013.01);
(Continued)

(58) Field of Classification Search
CPC .. H04N 5/2354; H04N 5/2351; H04N 5/2256; H04N 5/2252; A61B 90/30;
(Continued)

(56) References Cited

U.S. PATENT DOCUMENTS

| 8,361,775 B2 | 1/2013 | Flower |
| 8,448,867 B2 | 5/2013 | Liu et al. |

(Continued)

FOREIGN PATENT DOCUMENTS

| CN | 201974160 U | 9/2011 |
| EP | 2 859 837 A1 | 4/2015 |

(Continued)

OTHER PUBLICATIONS

International Search Report dated Feb. 10, 2017 for PCT/CA2016/051315.

(Continued)

*Primary Examiner* — Jason A Flohre
(74) *Attorney, Agent, or Firm* — Lee & Morse, P.C.

(57) ABSTRACT

An imaging device may include a first illumination port to output first light having a first illumination distribution at a target to illuminate the target, a second illumination port to output second light having a second illumination distribution at the target to illuminate the target, the second illumination distribution being substantially similar to the first illumination distribution at the target, the second illumination port being spaced apart from the first illumination port, the first and second illumination distributions being simultaneously provided to the target and overlapping at the (Continued)

target. The illumination from the first and second ports may be matched to a same aspect ratio and field of view coverage as the imaging field of view.

14 Claims, 30 Drawing Sheets

(51) Int. Cl.
*A61B 90/00* (2016.01)
*A61B 90/30* (2016.01)
*H04N 5/225* (2006.01)
*H04N 5/235* (2006.01)

(52) U.S. Cl.
CPC ......... *H04N 5/2256* (2013.01); *H04N 5/2351* (2013.01); *A61B 90/361* (2016.02); *A61B 2017/00477* (2013.01); *A61B 2090/306* (2016.02); *A61B 2090/309* (2016.02); *A61B 2090/3941* (2016.02)

(58) Field of Classification Search
CPC . A61B 46/10; A61B 90/361; A61B 2090/309; A61B 2090/3941; A61B 2017/00477; A61B 2090/306
See application file for complete search history.

(56) References Cited

U.S. PATENT DOCUMENTS

| | | | | |
|---|---|---|---|---|
| 2002/0156380 | A1* | 10/2002 | Feld | .................... A61B 5/0075 600/473 |
| 2003/0080193 | A1 | 5/2003 | Ryan et al. | |
| 2004/0186351 | A1* | 9/2004 | Imaizumi | ........... A61B 1/00009 600/160 |
| 2006/0094109 | A1* | 5/2006 | Trainer | .............. G01N 15/1456 435/288.7 |
| 2006/0250696 | A1 | 11/2006 | McGuire | |
| 2009/0285762 | A1 | 11/2009 | Flower | |
| 2010/0065641 | A1* | 3/2010 | Liu | .................... G06K 7/10831 235/462.32 |
| 2010/0155487 | A1 | 6/2010 | Liu et al. | |
| 2014/0071328 | A1 | 3/2014 | Miesak | |
| 2014/0078378 | A1 | 3/2014 | Demers et al. | |
| 2014/0186351 | A1 | 7/2014 | Britta et al. | |
| 2014/0187967 | A1* | 7/2014 | Wood | ................... A61B 5/0071 600/473 |
| 2015/0083932 | A1 | 3/2015 | Rizo et al. | |
| 2015/0381909 | A1* | 12/2015 | Butte | ..................... H04N 5/332 348/68 |
| 2016/0041098 | A1* | 2/2016 | Hirawake | .......... G01N 21/6456 250/459.1 |
| 2016/0044253 | A1* | 2/2016 | Dainty | ................. H04N 5/2254 348/349 |

FOREIGN PATENT DOCUMENTS

| | | |
|---|---|---|
| WO | WO 2007/081707 A2 | 7/2007 |
| WO | WO 2013/160279 A1 | 10/2013 |
| WO | WO 2014/176375 A2 | 10/2014 |
| WO | WO 2016 055837 A1 | 4/2016 |

OTHER PUBLICATIONS

International Preliminary Report on Patentability dated May 24, 2018 for International Application No. PCT/CA2016/051315 filed on Nov. 10, 2016, nine pages.

Australian Examination Report No. 1 dated Jun. 28, 2018 for Australian Application No. 2016351730 filed on Nov. 10, 2016, five pages.

Canadian Office Action dated Feb. 19, 2019 for corresponding Canadian Application No. 2,998,920 filed Mar. 16, 2018, four pages.

Australian Office Action dated May 10, 2019 for corresponding Australian Application No. 2016351730.

Extended European Search Report dated May 7, 2019 for corresponding European Application No. 16863277.6.

* cited by examiner

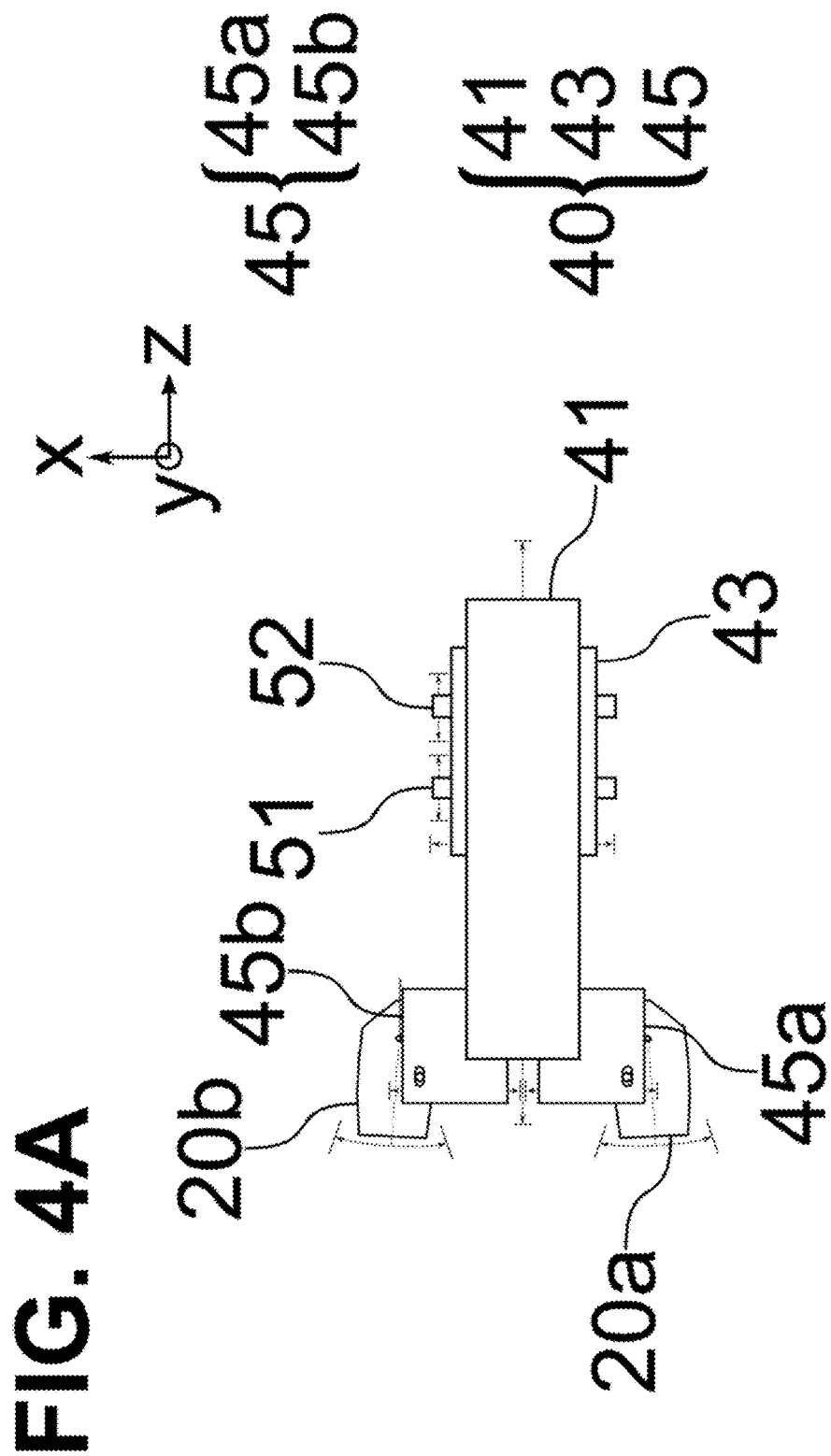

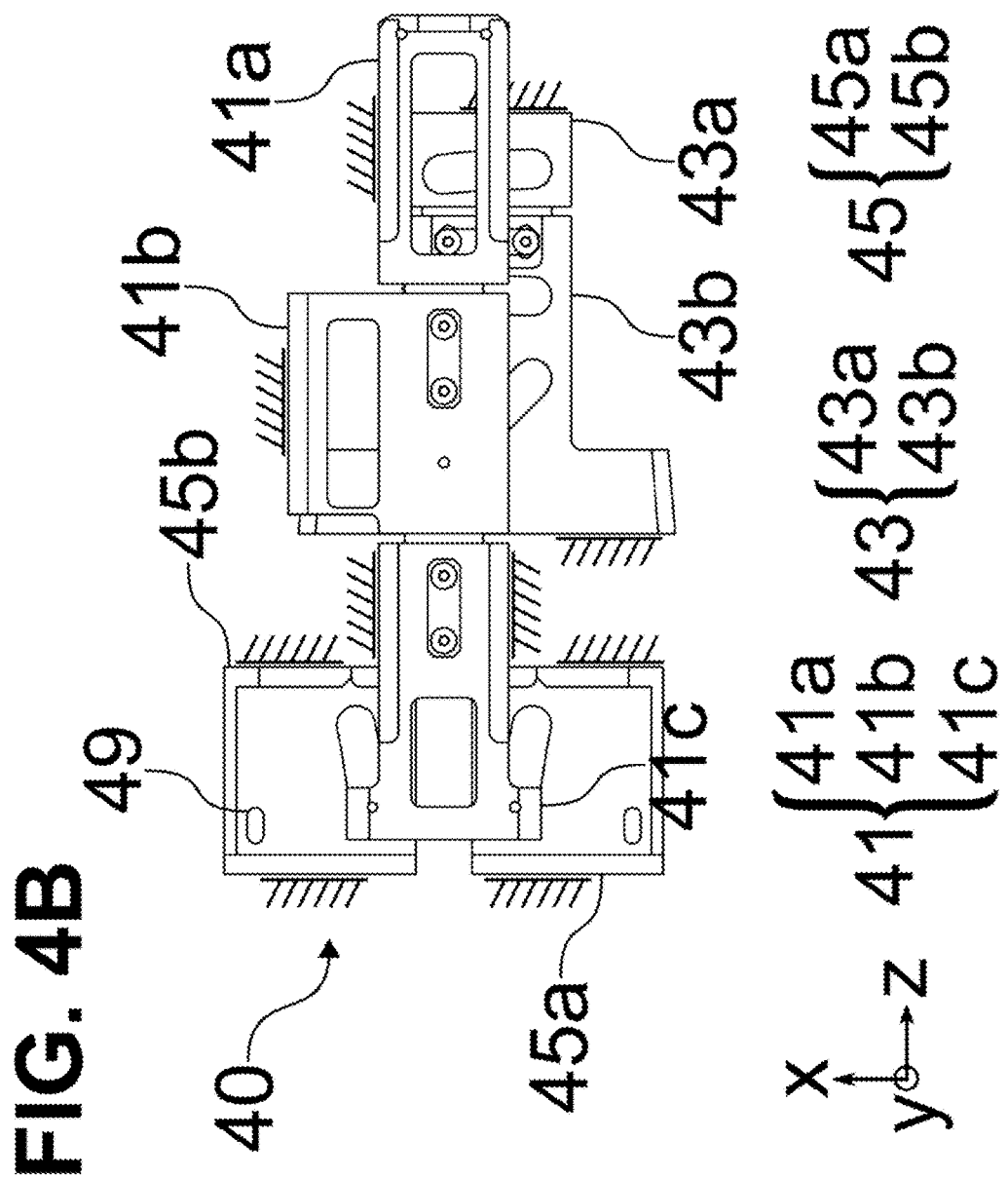

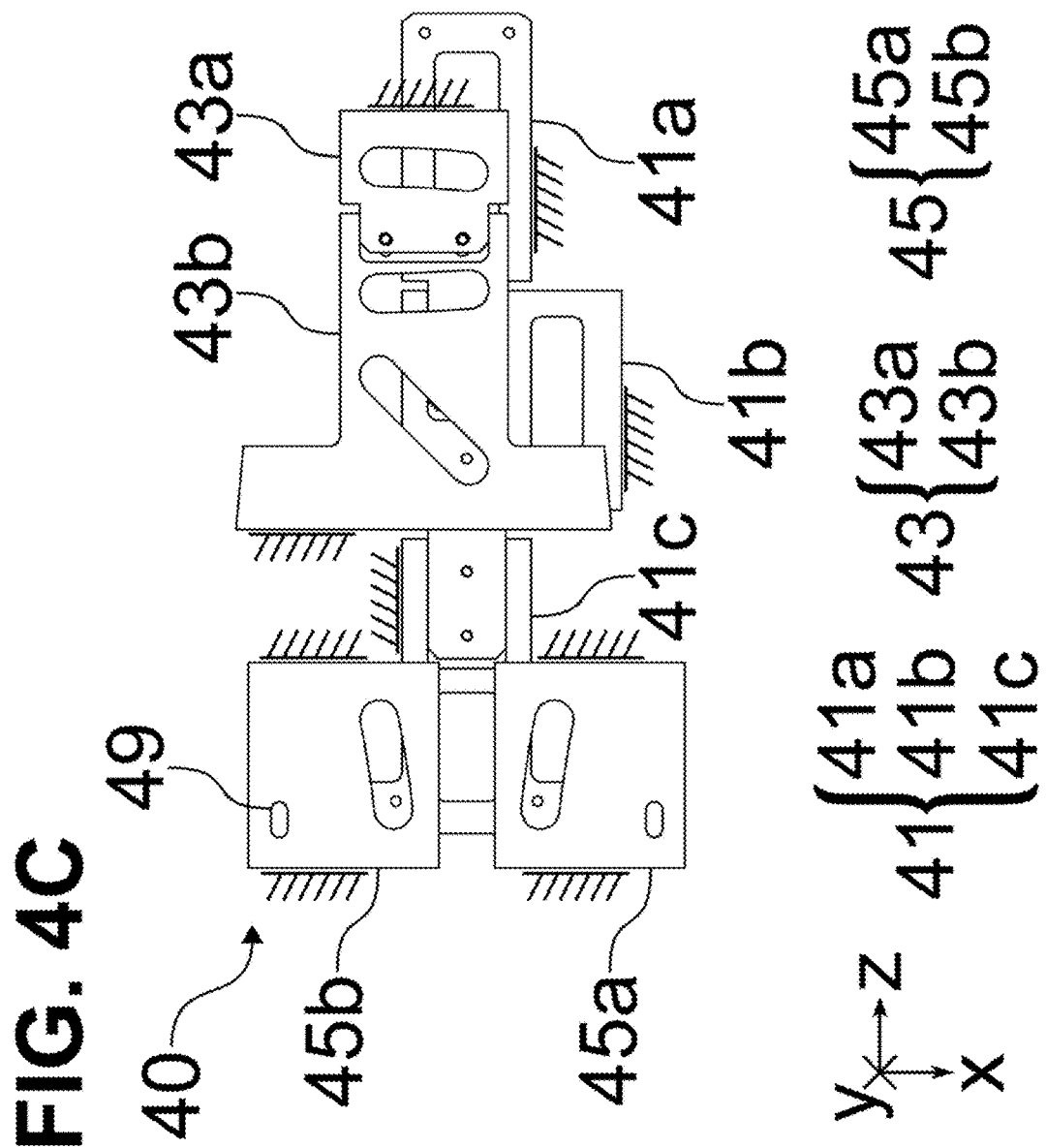

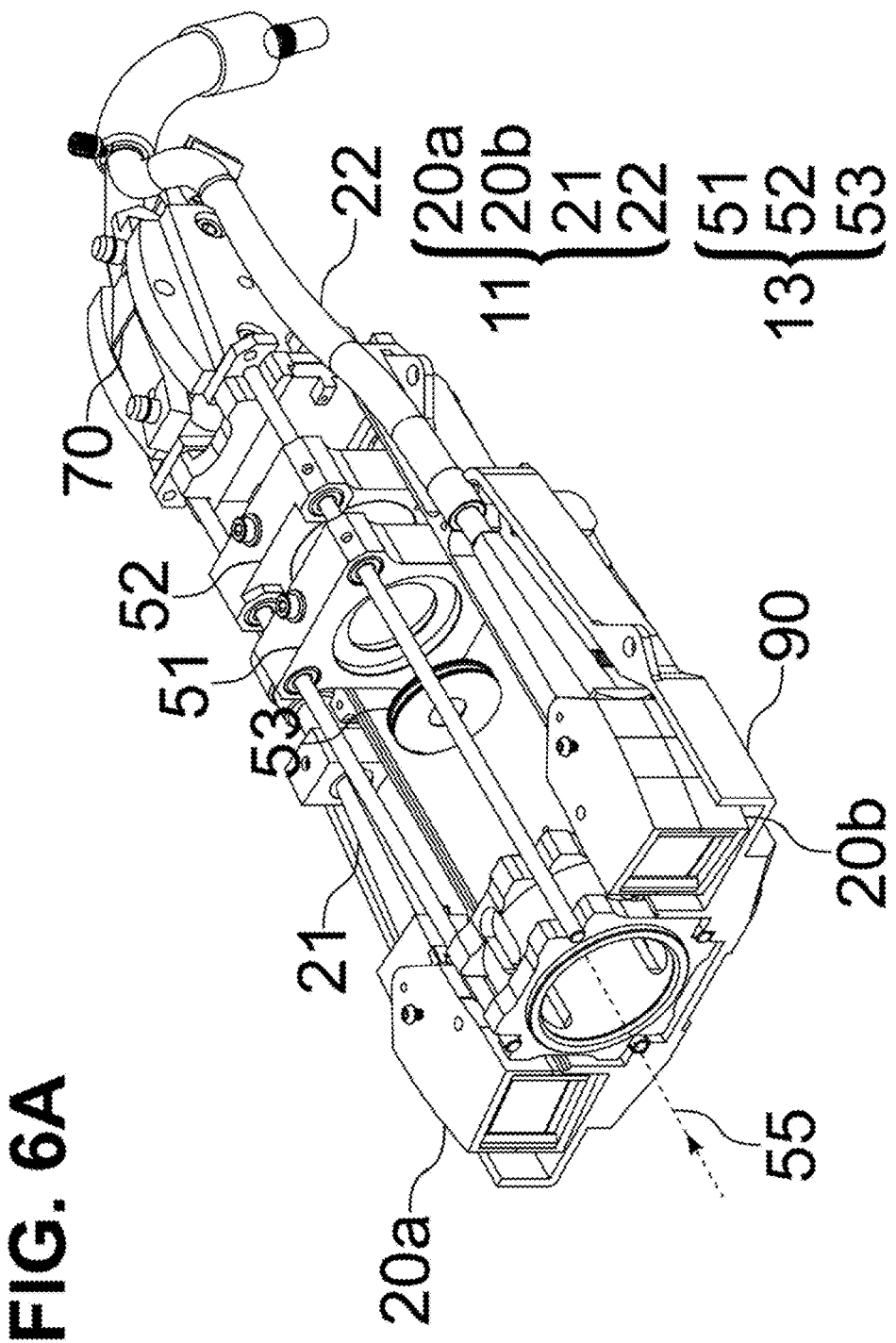

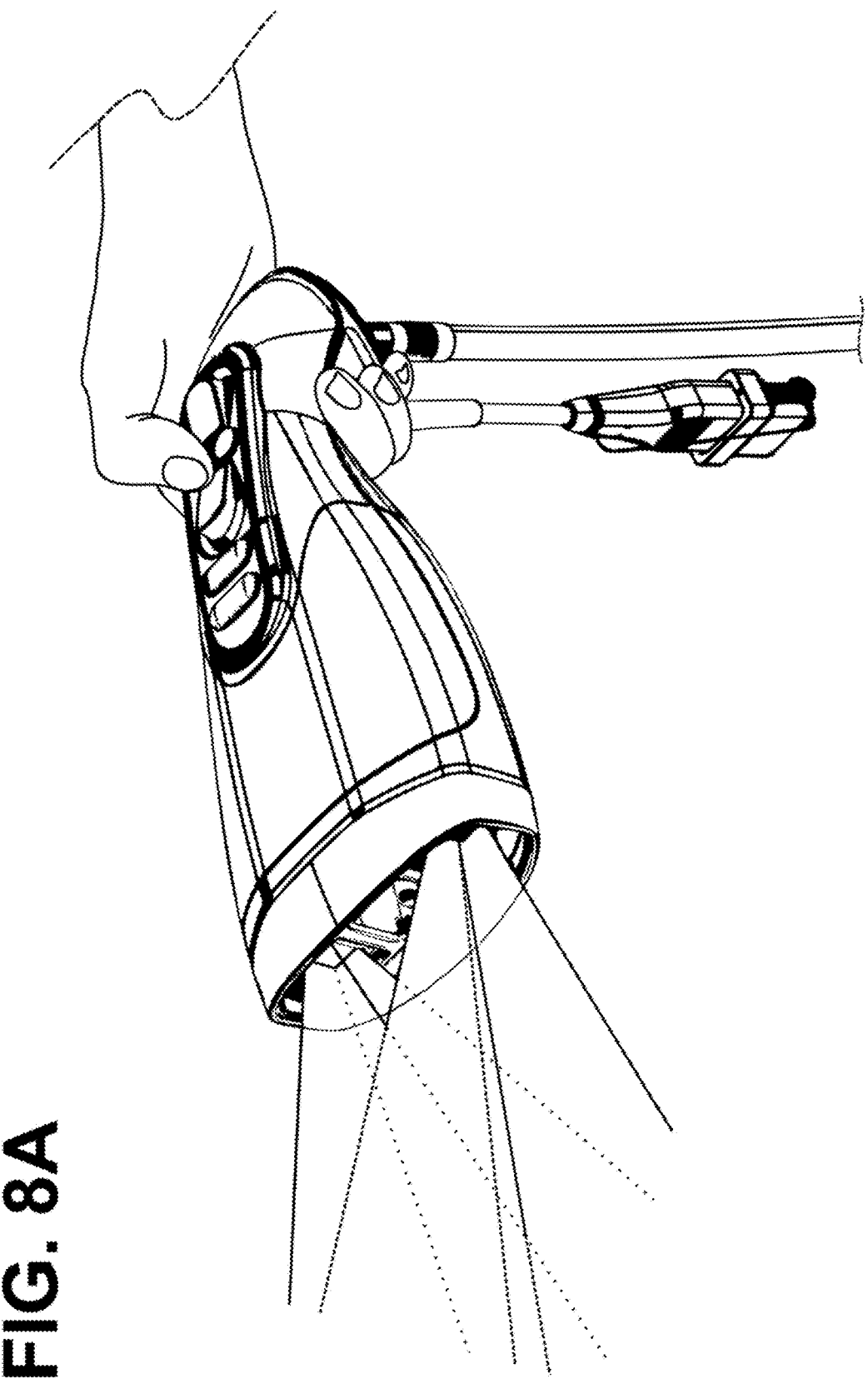

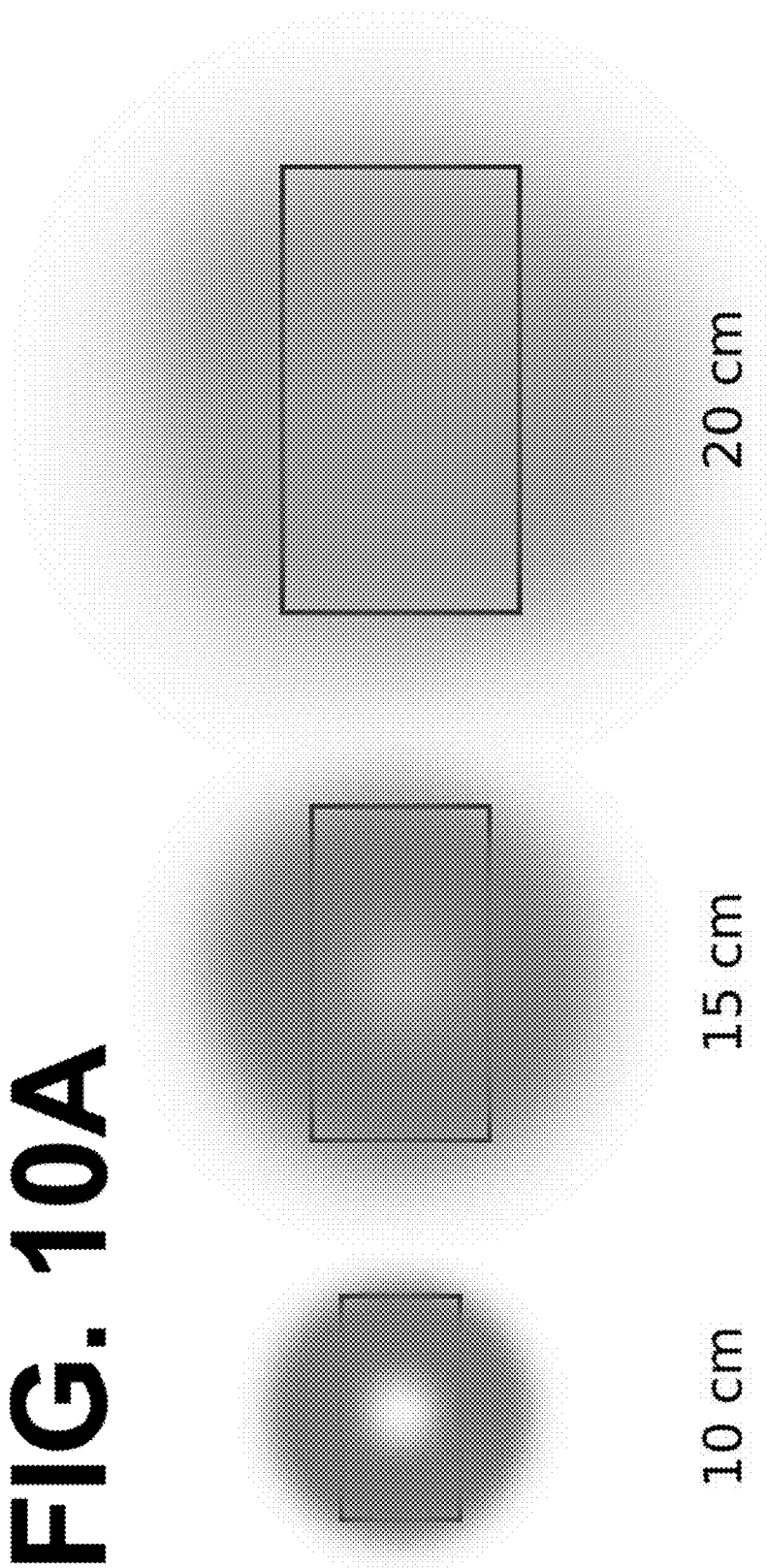

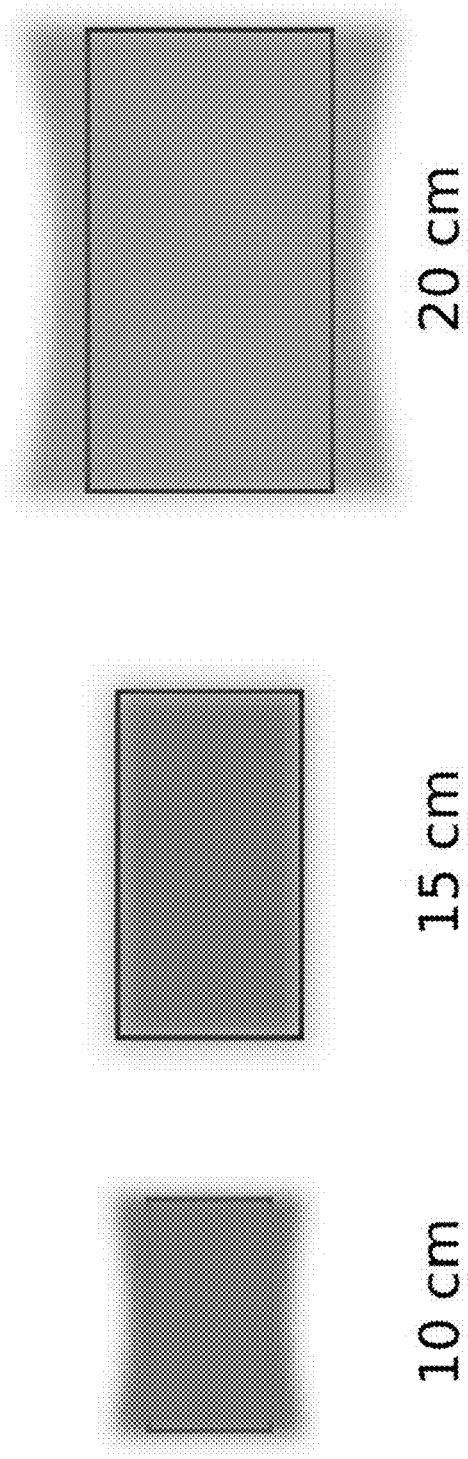

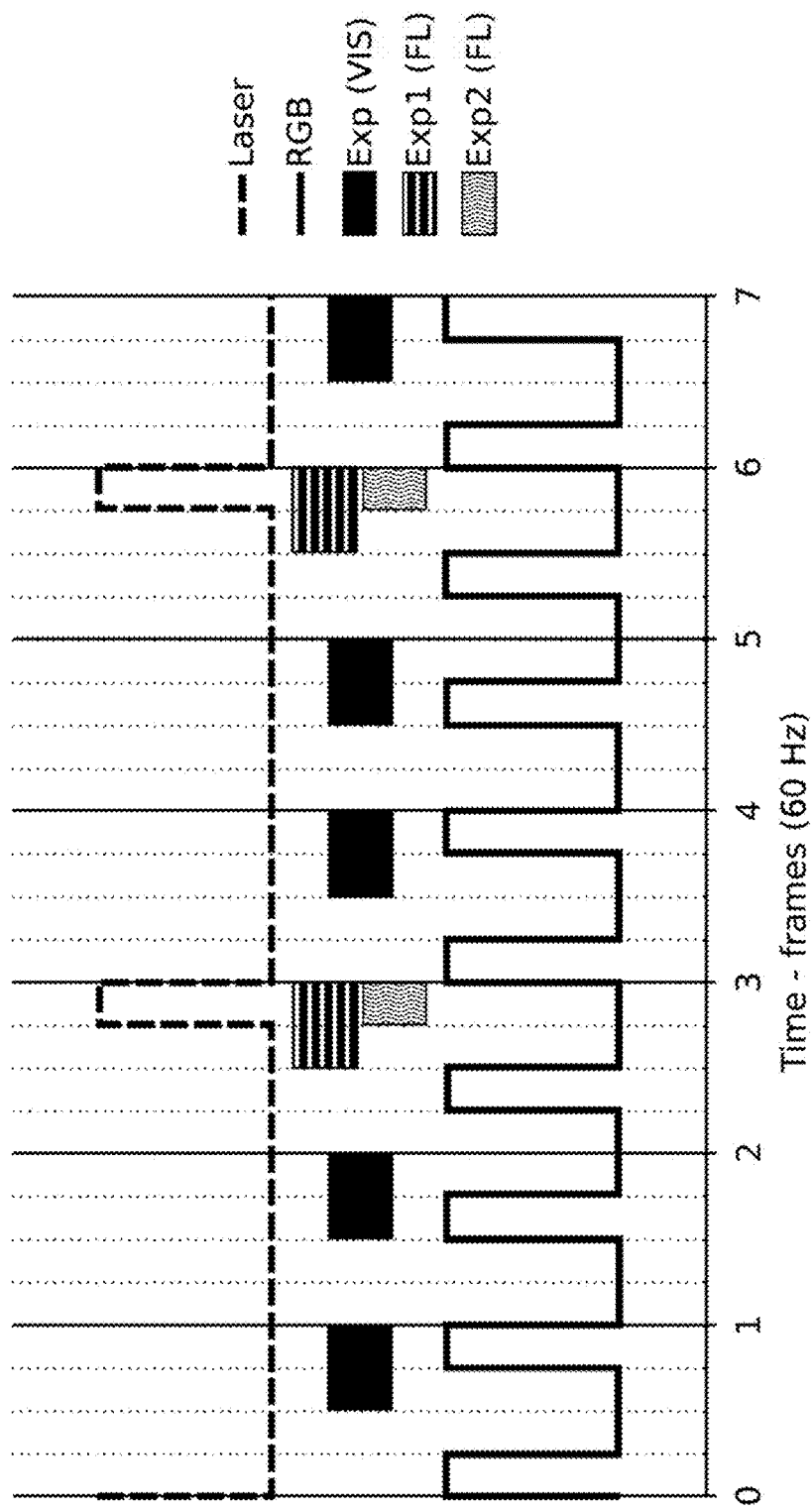

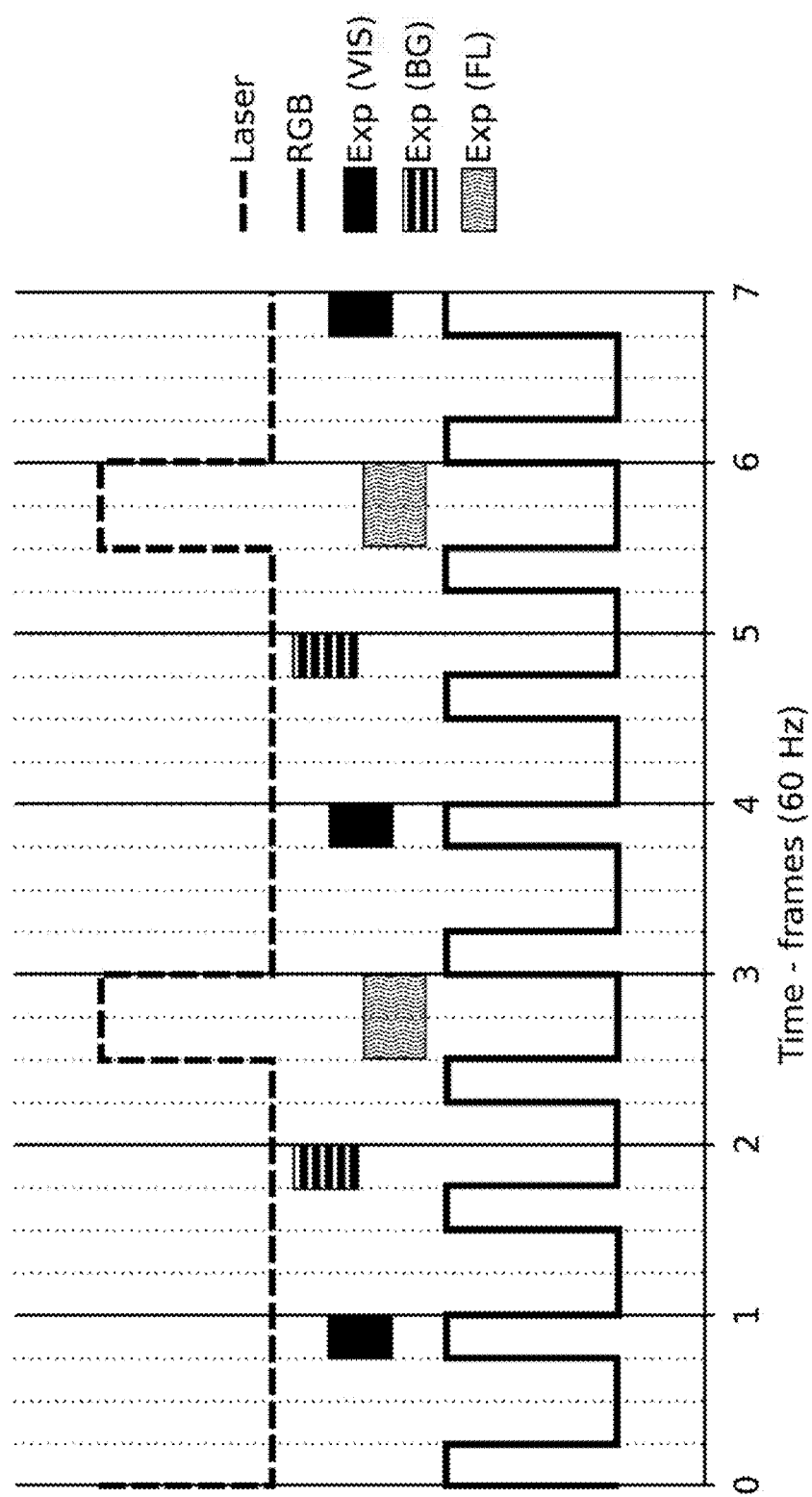

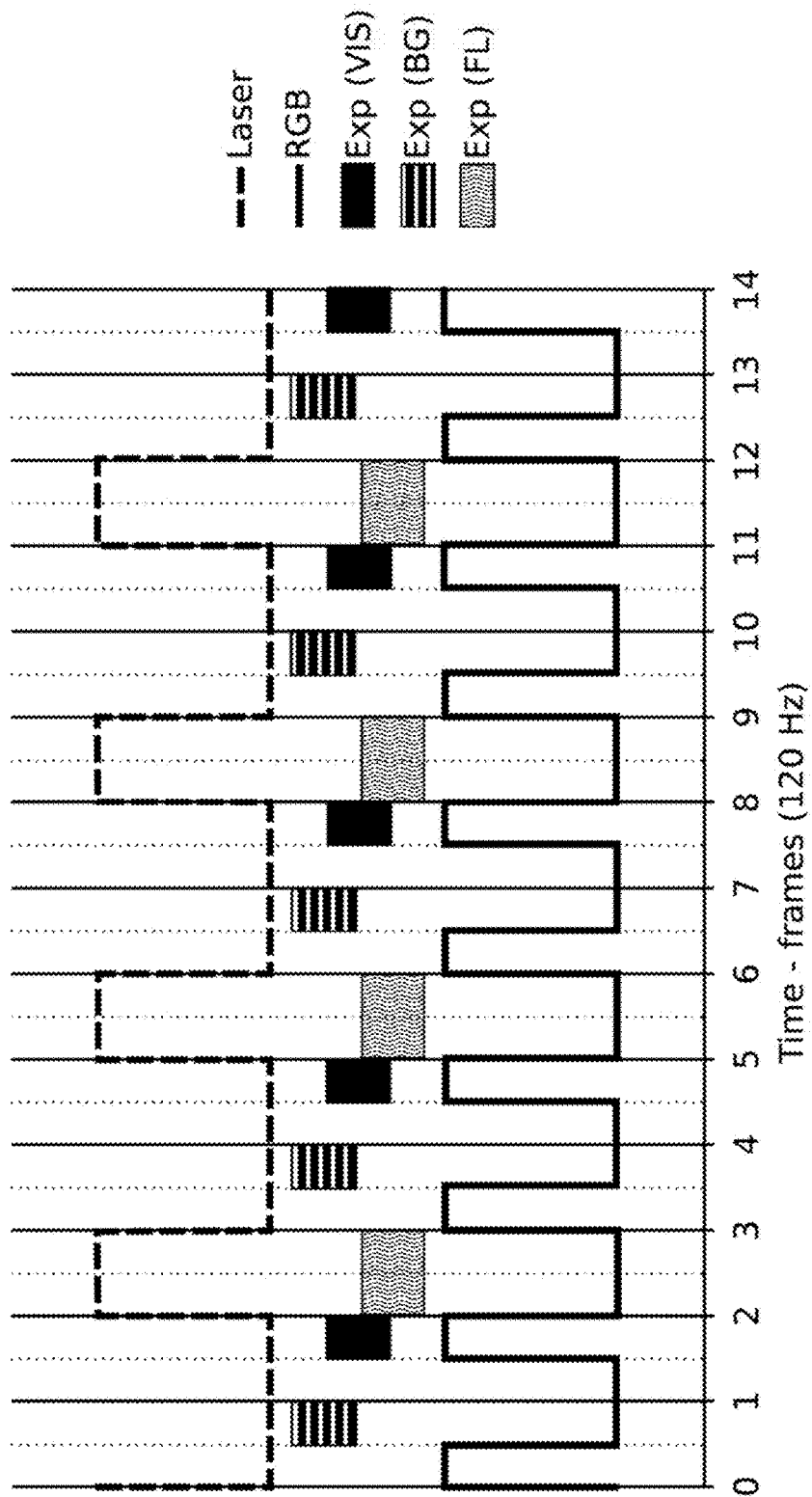

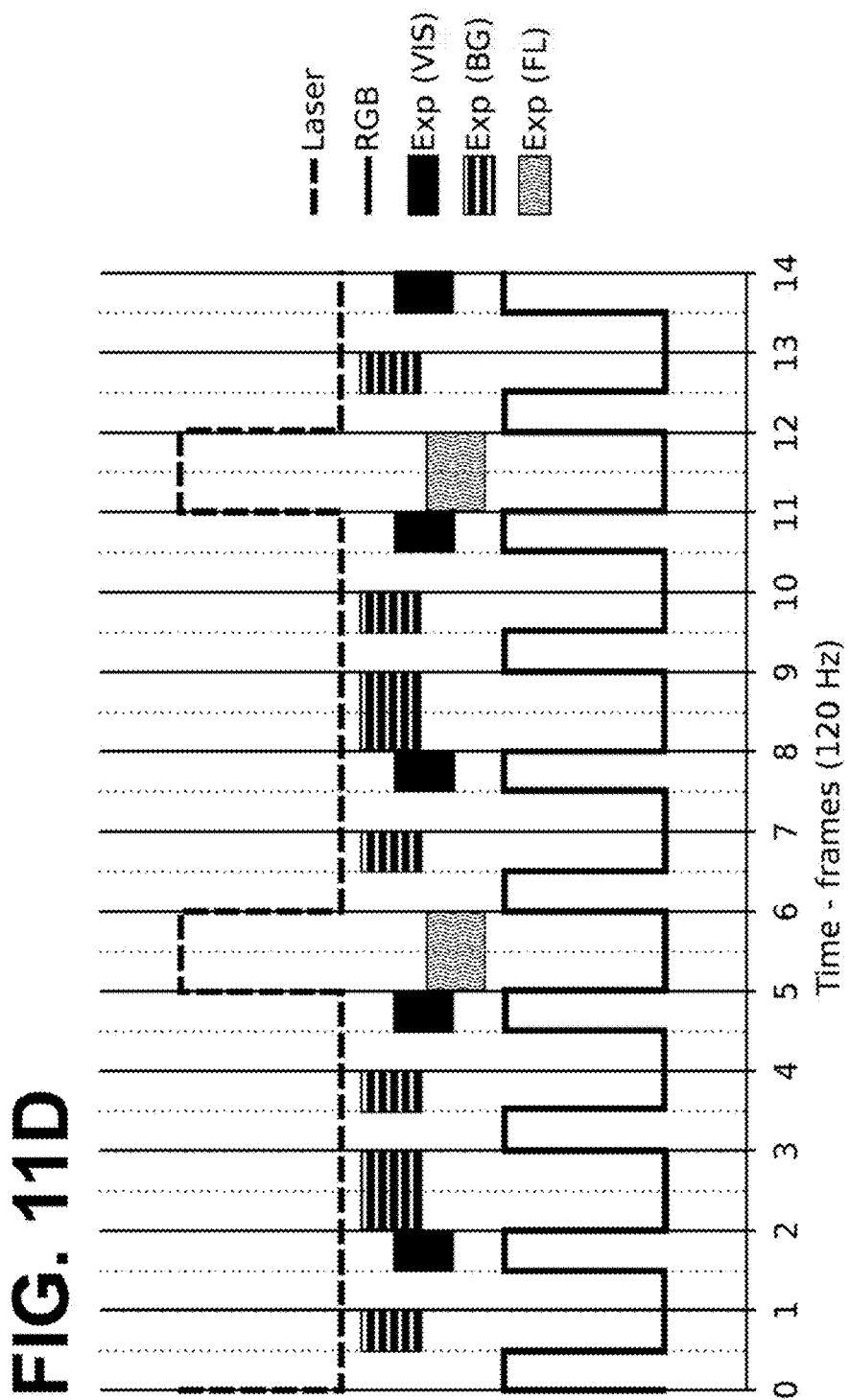

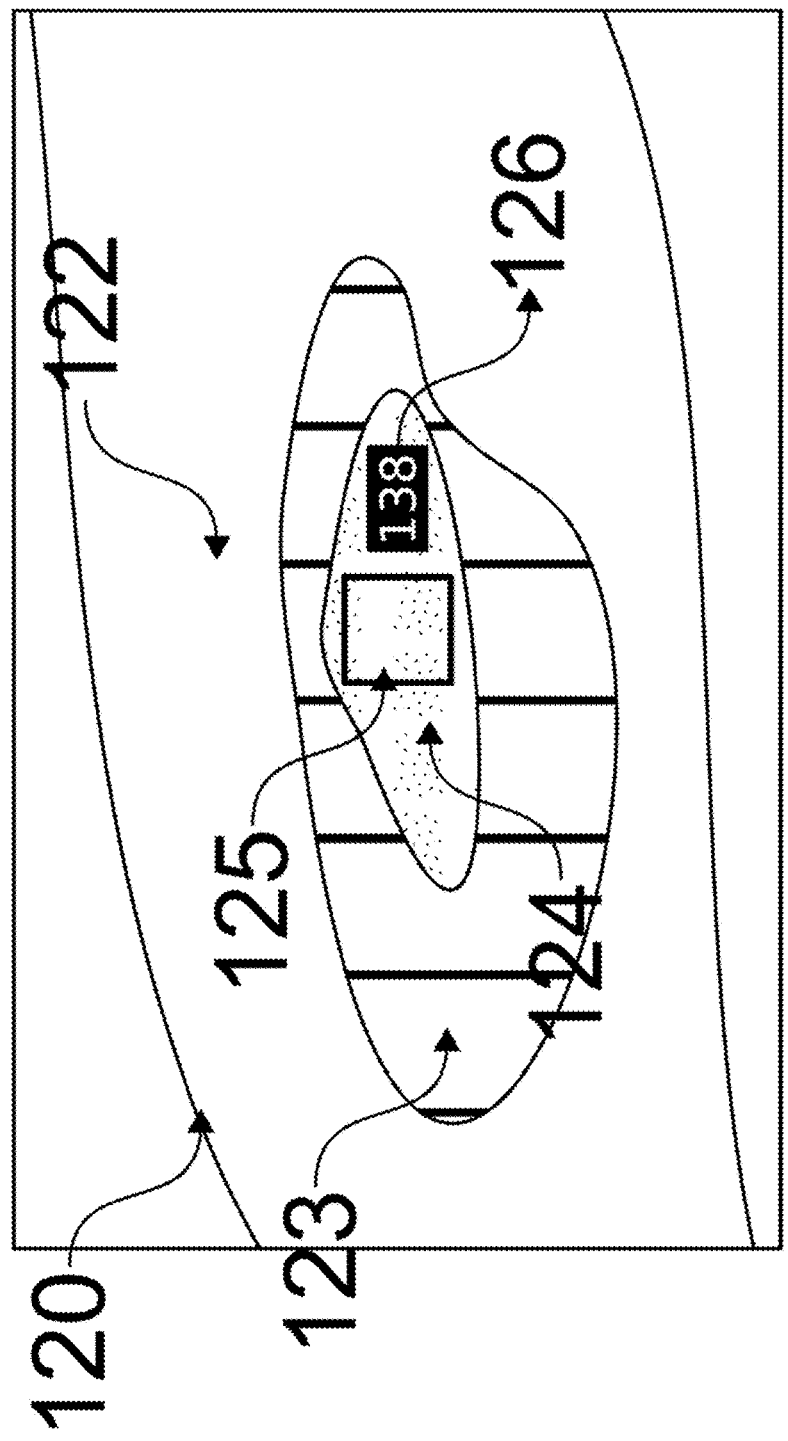

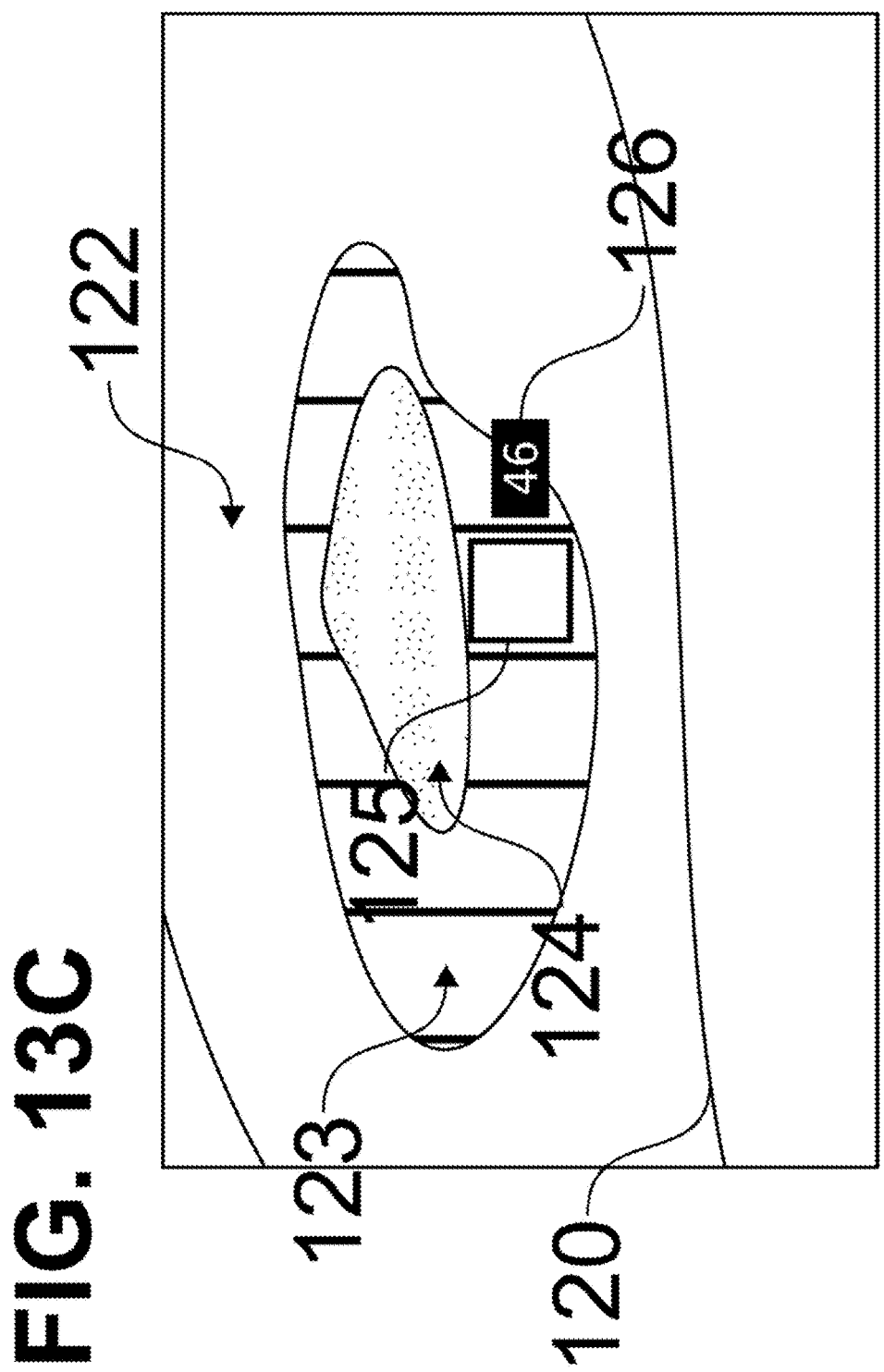

SYSTEMS AND METHODS FOR ILLUMINATION AND IMAGING OF A TARGET

REFERENCE TO RELATED APPLICATIONS

This application claims priority to U.S. Provisional Application Ser. No. 62/255,024 filed Nov. 13, 2015, titled "Systems and Methods for Illumination and Imaging of a Target," which is hereby incorporated by reference in its entirety.

TECHNICAL FIELD

The present disclosure relates generally to the field of illumination and imaging. More specifically, the disclosure relates to illumination and imaging of a target material.

BACKGROUND

Illumination is an important component of imaging systems such as, for example, broadband imaging systems with self-contained illumination. In many applications of imaging systems, such as in medical imaging, it may be challenging to achieve even, full field illumination of the imaging field of view, aid also to provide a sufficient intensity of illumination to yield a sufficiently strong imaging signal. Conforming the illumination profile to match the imaging field of view is one method of conserving illumination power, while multiple illumination ports may be used to provide even illumination across the field of view. Conventional illumination projection in imaging systems may feature anamorphic projection to match the imaging field of view, but typically only feature a single illumination port and are not configured for close working distances. Single port illumination systems result in substantial shadowed regions obscuring vision when illuminating complex topography such as, for example, human anatomical structures or other biological materials. Existing designs for field surgical imaging and illumination devices may make use of multiple illumination ports to minimize shadowed regions, such as a ring light surrounding the imaging optics, but these designs waste excess illumination outside of the field of view and fail to achieve even illumination of the field of view over a range of working distances.

SUMMARY

One or more embodiments are directed to an illumination module for use in an imaging system having an imaging field of view for imaging a target, the illumination module including a first illumination port to output a first light beam having a first illumination distribution at the target to illuminate the target and a second illumination port to output a second light beam having a second illumination distribution at the target to illuminate the target. The second illumination distribution may be substantially similar to the first illumination distribution at the target, the second illumination port being spaced apart from the first illumination port, the first and second illumination distributions being simultaneously provided to the target and overlapping at the target, wherein the illumination from the first and second ports is matched to a same aspect ratio and field of view coverage as the imaging field of view.

Light from the first and second illumination ports may respectively overlap to provide uniform illumination over a target field of view.

The illumination module may include a steering driver to simultaneously steer the first and second illumination ports through different fields of view.

Each of the first and second illumination ports may include a lens module having at least one fixed lens, a steerable housing, and at least one lens mounted in the steerable housing, the steerable housing being in communication with the steering driver.

The illumination module may include an enclosure, the enclosure housing the first and second illumination ports and the steering driver.

The enclosure may be a hand held enclosure and may include a control surface including activation devices to control the steering driver.

Each of the first and second illumination distributions may be a rectangular illumination distribution.

Each of the first and second illumination ports may include a lens module having two pairs of cylindrical lenses.

The first and second illumination ports may be symmetrically offset from a long dimension midline of the rectangular illumination distribution.

One or more embodiments are directed to an imaging device having an imaging field of view, the imaging device including a first illumination port to output first light having a first illumination distribution at a target to illuminate the target, a second illumination port to output second light having a second illumination distribution at the target to illuminate the target, the second illumination distribution being substantially similar to the first illumination distribution at the target, the second illumination port being spaced apart from the first illumination port, the first and second illumination distributions being simultaneously provided to the target and overlapping at the target, wherein the illumination from the first and second ports is matched to a same aspect ratio and field of view coverage as the imaging field of view, and a sensor to detect light from the target.

The imaging device may include an enclosure, the enclosure housing the first and second illumination ports, and the sensor.

The imaging device may include a steering driver to simultaneously steer the first and second illumination ports through different fields of view.

The imaging device may include an imaging element to focus light onto the sensor, wherein the steering driver is to move the imaging element in synchrony with steering of the first and second illumination ports.

The steering driver may be in the enclosure and the enclosure may include a control surface including activation devices to control the steering driver.

The enclosure may have a hand held enclosure having a form factor that allows a single hand to control the control surface and illumination of the target from multiple orientations.

The imaging device may include an illumination source to output light to the first and second illumination ports, the illumination source being outside the enclosure.

The illumination source may output visible light and/or excitation light to the first and second illumination ports.

The sensor may be a single sensor that is to detect light from the target resulting from illumination by visible light and excitation light.

The imaging device may include a wavelength-dependent aperture upstream of the sensor, the wavelength-dependent aperture to block visible light outside a central region.

The imaging device may include a video processor box, the video processor box being outside the enclosure.

The illumination source may be integral with the video processor box.

One or more embodiments are directed to a method of examining a target, the method including simultaneously illuminating the target with a first light output having a first illumination distribution at the target and with a second light output having a second illumination distribution at the target, the second illumination distribution being substantially similar to the first illumination distribution, the first and second illumination distributions overlapping at the target, wherein the illumination on the target is matched to the same aspect ratio and field of view coverage as an imaging field of view.

The method may include simultaneously steering the first and second light outputs through different fields of view.

The method may include receiving light from the target and focusing light onto a sensor using an imaging element, the imaging element being moved in synchrony with simultaneous steering of the first and second light outputs.

One or more embodiments are directed to a drape for use with an imaging device, the drape including a barrier material enveloping the imaging device, a drape window frame defining an opening in the barrier material, a drape lens in the opening in the barrier material, and an interface integral with the drape window frame to secure the drape lens to a window frame of the imaging device.

The drape may be insertable into the window frame of the imaging device.

The interface may include two clamps integrated symmetrically on respective opposing sides of the drape window frame.

The two clamps are on a top and a bottom of the drape window frame.

One or more embodiments are directed to a processor to image a target, the processor to, within a period, turn on an excitation light source to generate an excitation pulse to illuminate the target, turn on a white light source to generate a white pulse to illuminate the target such that the white pulse does not overlap the excitation pulse and the white pulse is generated at least twice within the period, expose an image sensor for a fluorescent exposure time during the excitation pulse, expose the image sensor for a visible exposure time during at least one white pulse, detect outputs from the image sensor, compensate for ambient light, and output a resultant image.

To compensate for ambient light, the processor may expose a first set of sensor pixel rows of the image sensor for a fraction of the fluorescent exposure time for a first set of sensor pixel rows; and expose a second set of sensor pixel rows of the image sensor for all of the fluorescent exposure time, the first and second sets to detect at least one different color from the other.

The fraction may be ½.

The processor may determine the fluorescent signal F using the following equation:

$$F = 2 * Exp2 - Exp1,$$

where Exp1 is a signal output during the fraction of fluorescent exposure time and Exp2 is a signal output during all of the fluorescent exposure time.

The fraction of the exposure time may equal a width of the excitation pulse.

The visible exposure time may be longer than a width of the at least one white pulse.

The visible exposure time may be for one white pulse within the period.

The visible exposure time may be for two white pulses within the period.

To compensate for ambient light, the processor may expose the image sensor for a background exposure time when target is not illuminated at least once within the period.

One or more embodiments are directed a method for imaging a target, within a period, the method including generating an excitation pulse to illuminate the target, generating a white pulse to illuminate the target such that the white pulse does not overlap the excitation pulse and the white pulse is generated at least twice within the period, exposing an image sensor for a fluorescent exposure time during the excitation pulse, exposing the image sensor for a visible exposure time during at least one white pulse, detecting outputs from the image sensor, compensating for ambient light, and outputting a resultant image.

Compensating for ambient light may include exposing a first set of sensor pixel rows of the image sensor for a fraction of the fluorescent exposure time and exposing a second set of sensor pixel rows of the image sensor for all of the fluorescent exposure time, the first and second sets to detect at least one different color from the other.

Compensating for ambient light may include exposing the image sensor for a background exposure time when target is not illuminated at least once within the period.

Generating the excitation pulse may include providing uniform, anamorphic illumination to the target.

Providing uniform, anamorphic illumination to the target includes overlapping illumination from at least two illumination ports.

One or more embodiments are directed to a method of displaying fluorescence intensity in an image, the method including displaying a target reticle covering a region of the image, calculating a normalized fluorescence intensity within the target reticle, and displaying the normalized fluorescence intensity in a display region associated with the target.

The display region may be projected onto the target.

The normalized fluorescence intensity may include a single numerical value and/or a historical plot of normalized fluorescence intensities.

One or more embodiments are directed to a kit, including an illumination module including at least two illumination ports spaced apart from one another, first and second illumination distributions to being simultaneously provided to a target and to overlap at the target, and an imaging module including a sensor to detect light from the target.

The kit may include an enclosure to enclose the illumination module and the imaging module.

One or more embodiments are directed to a fluorescence imaging agent for use in the imaging device and methods as described herein. In one or more embodiments, the use may comprise blood flow imaging, tissue perfusion imaging, lymphatic imaging, or a combination thereof, which may occur during an invasive surgical procedure, a minimally invasive surgical procedure, a non-invasive surgical procedure, or a combination thereof. The fluorescence agent may be included in the kit described herein.

In one or more embodiments, the invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

In one or more embodiments, the minimally invasive or the non-invasive surgical procedure may comprise a wound care procedure.

In one or more embodiments, the lymphatic imaging may comprise identification of a lymph node, lymph node drainage, lymphatic mapping, or a combination thereof. The lymphatic imaging may relate to the female reproductive system.

BRIEF DESCRIPTION OF THE DRAWINGS

Features will become apparent to those of ordinary skill in the art by describing in detail exemplary embodiments with reference to the attached drawings in which:

FIG. 4A illustrates a schematic view of a linkage for synchronous focusing of the imaging system and steering of the illumination system according to embodiments;

FIGS. 4B and 4C illustrate a bottom view and a top view, respectively, of a linkage for synchronous focusing of the imaging system and steering of the illumination system according to embodiments;

FIGS. 6A and 6B illustrate a perspective top view and a perspective bottom view of an illumination and imaging system according to an embodiment;

FIGS. 8A and 8B illustrate perspective views of different exemplary positions in which the system may be used;

FIGS. 10A to 10C illustrate illumination distributions for different illumination configurations;

FIG. 11A illustrates a timing diagram for visible and excitation illumination according to an embodiment;

FIG. 11B illustrates a timing diagram for visible and excitation illumination according to an embodiment;

FIG. 11C illustrates a timing diagram for visible and excitation illumination according to an embodiment;

FIG. 11D illustrates a timing diagram for visible and excitation illumination according to an embodiment;

FIGS. 12A to 12C illustrate pixel layout and an interpolation scheme according to an embodiment;

FIGS. 13A to 13C illustrate diagrams of an embodiment of a display method output when a target reticle is placed over regions of no normalized fluorescence intensity, high relative normalized fluorescence intensity, and moderate relative normalized fluorescence intensity, respectively;

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. Various devices, systems, methods, processors, kits and imaging agents are described herein. Although at least two variations of the devices, systems, methods, processors, kits and imaging agents are described, other variations may include aspects of the devices, systems, methods, processors, kits and imaging agents described herein combined in any suitable manner having combinations of all or some of the aspects described.

Generally, corresponding or similar reference numbers will be used, when possible, throughout the drawings to refer to the same or corresponding parts.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Figure 1:
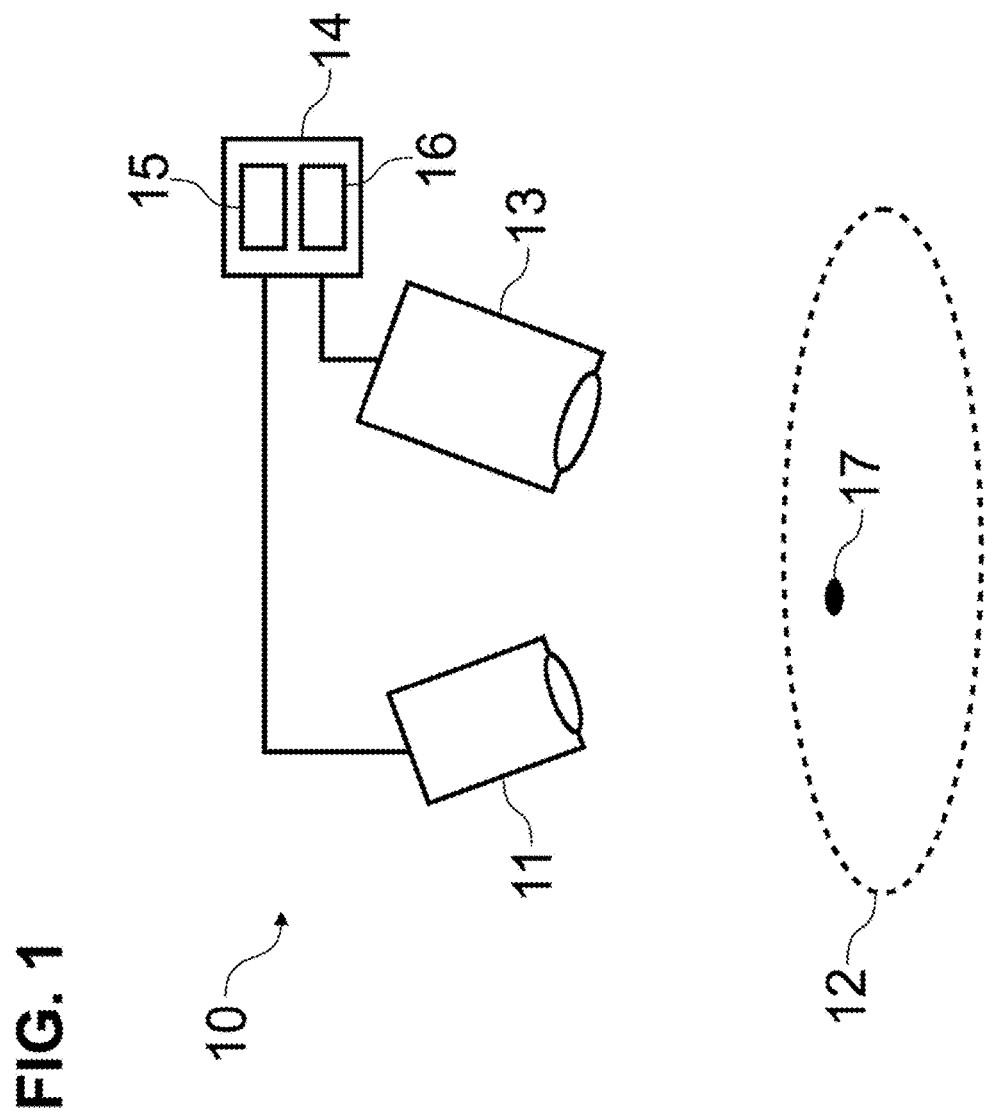
FIG. 1 illustrates a schematic view of a system for illumination and imaging according to an embodiment.

FIG. 1 illustrates a schematic view of an illumination and imaging system 10 according to an embodiment. As may be seen therein, the system 10 may include an illumination module 11, an imaging module 13, and a video processor/illuminator (VPI) 14. The VPI 14 may include an illumination source 15 to provide illumination to the illumination module 11 and a processor assembly 16 to send control signals and to receive data about light detected by the imaging module 13 from a target 12 illuminated by light output by the illumination module 11. The illumination source 15 may output light at different waveband regions, e.g., white (RGB) light, excitation light to induce fluorescence in the target 12, and so forth, depending on characteristics to be examined and the material of the target 12. Light at different wavebands may be output by the illumination source simultaneously or sequentially. The illumination and imaging system 10 may be used, for example, to facilitate a surgical procedure. The target 12 may be a topographically complex target, e.g., a biological material including tissue, an anatomical structure, other objects with contours and shapes resulting in shadowing when illuminated, and so forth. The VPI 14 may record, process, display, and so forth, the resulting images and associated information.

Figure 2:
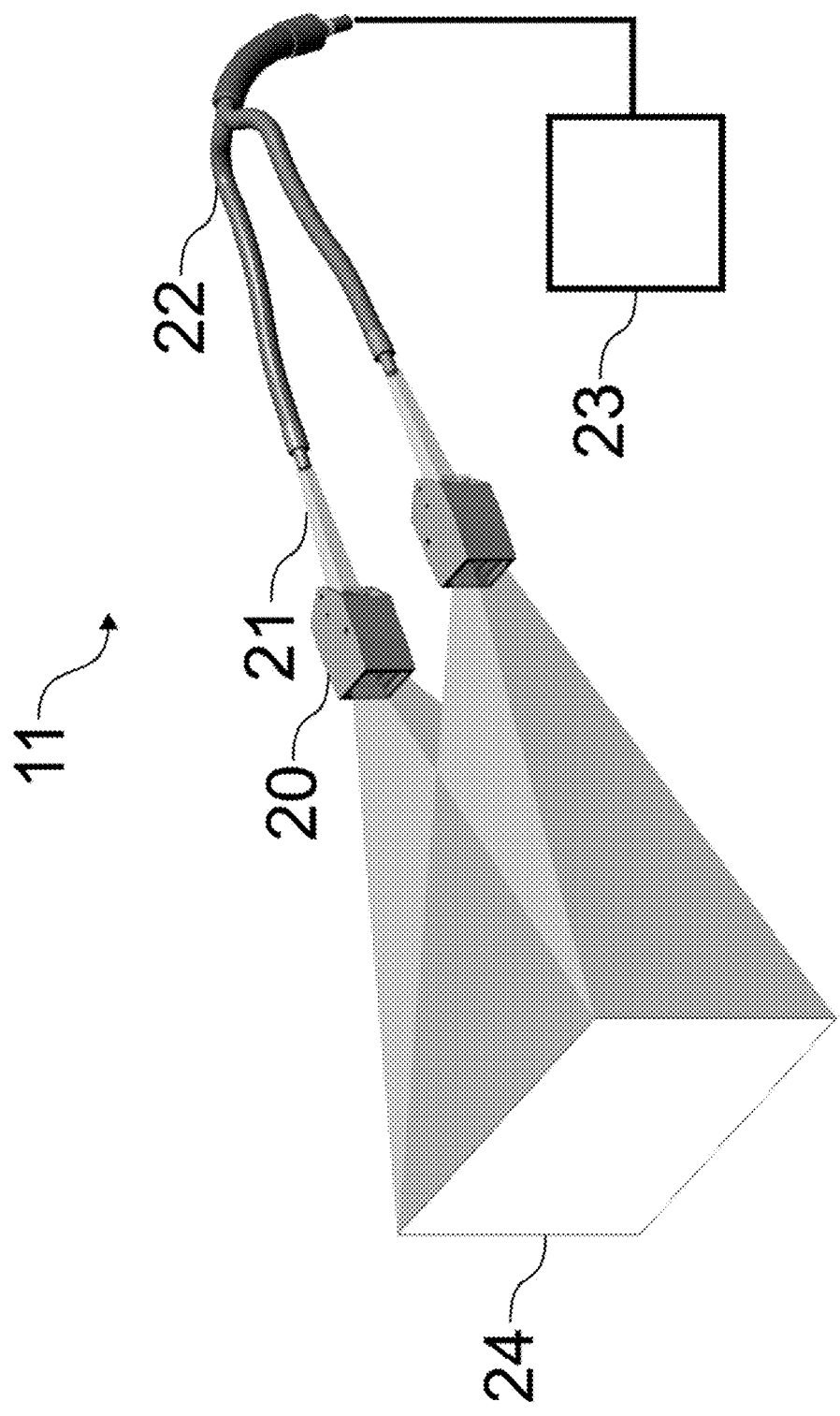
FIG. 2 illustrates a schematic view of an illumination module according to an embodiment.

FIG. 2 illustrates a schematic perspective view of the illumination module 11 of FIG. 1 according to an embodiment. As may be seen therein, the illumination module 11 may include at least two illumination ports directing illumination from an illumination source 23, which may be included in the VPI box 14, to for example a rectangular target field 24. Each illumination port is to provide illumination over the target field 24, such that the light overlaps, e.g., substantially or completely, at the target material 12 (shown in FIG. 1). More than two illumination ports may be used. The illumination distributions are substantially similar and substantially overlap at the target 12 to provide uniform illumination of the target 12. The use of at least two illumination ports reduces the effect of shadowing due to anatomical topography, and aids in providing uniform illumination over the target field 24. Directing illumination from the illumination module 11 to a rectangular target field 24 allows matching the region of illumination to a rectangular imaging field of view, which aids in providing uniform illumination and enhances efficiency of the illumination module by reducing extraneous illumination. Matching the illumination field to the imaging field of view also provides a useful indication of the location and extent of the anatomical region currently being imaged.

In some embodiments, a light pipe may be used to achieve mixing of the illumination light in order to yield a uniform illumination profile. Mixing of the illumination light by a light pipe may remove the influence of the structure of the light source on the illumination profile, which could otherwise adversely affect uniformity of the illumination profile. For example, using a light pipe to mix the illumination light output from a fiber optic light guide may remove images of the structure of the individual optical fibers from the illumination profile. In some embodiments, a rectangular light pipe may be used to conserve illumination power while matching the illumination profile to a rectangular imaging field of view. In some embodiments, a light pipe material with a high index of refraction for both visible light and near infrared light, such as optical glass material N-SF11, may be used for high efficiency of illumination power transmission.

According to some embodiments, a rectangular light pipe with an aspect ratio matching the aspect ratio of the imaging field of view (e.g., both aspect ratios being 16:9) may be used in conjunction with rotationally symmetric illumination optic elements.

According to some embodiments, a rectangular light pipe with a different aspect ratio than the imaging field of view (e.g., a square light pipe along with a 16:9 imaging field of view aspect ratio) may be used in conjunction with cylindrical illumination optic elements. Cylindrical optic elements may be used to separately conform one or both dimensions of the rectangular illumination profile to match the aspect ratio of the imaging field of view.

Depending on the desired system requirements for range of working distance and illumination uniformity various approaches may be used for matching the illumination to a rectangular imaging field of view. For example, applications with high requirements for range working distance and illumination uniformity may necessitate use of illumination optics that are steered dynamically to adequately match the illumination to the imaging field of view, while applications with lower requirements may be served with fixed illumination optics to match the illumination to the field of view.

In some embodiments, one or more illumination optic elements may be rotated by a driver in order to steer the illumination.

In some embodiments, one or more illumination optic elements may be translated perpendicular to the imaging optic axis by a driver in order to steer the illumination.

In some embodiments, one or more illumination optic elements may be configured to provide some distortion in the illumination profile, in order to account for distortion inherent to the accompanying imaging system.

In some embodiments, uniform illumination of the imaging field of view over a specified range of working distances may be achieved with a fixed location and orientation of the illumination optics. The offset distance of the illumination optics from the imaging optic axis may be configured, along with the orientation of the of the illumination optics, in order to optimize matching of the illumination profile to the imaging field of view at a working distance within the specified range of working distances while also maintaining substantial matching of the illumination profile to the imaging field of view at other working distances within the specified range.

As is illustrated in FIG. 2, each illumination port may include a lens module 20, a connecting cable 22 connected to the illumination light source 23, and a light pipe 21 adapting a high numerical aperture of the connecting cable 22 to a lower numerical aperture of the lens module 20. The lens module 20 may be steerable, as described in detail below. In some scenarios, acceptable performance may be achievable without steering. In other words, an illumination module, and imaging device having the same, that provides a illumination having a rectangular form factor that matches the field of view of the imaging system using at least two illumination ports in which each port produces a gradient of illumination such that the sum illumination flux in the object plane is reasonably the same at each point in the illumination field, e.g., provides uniform illumination over the imaging field of view, alone may be sufficient.

Figure 3A:
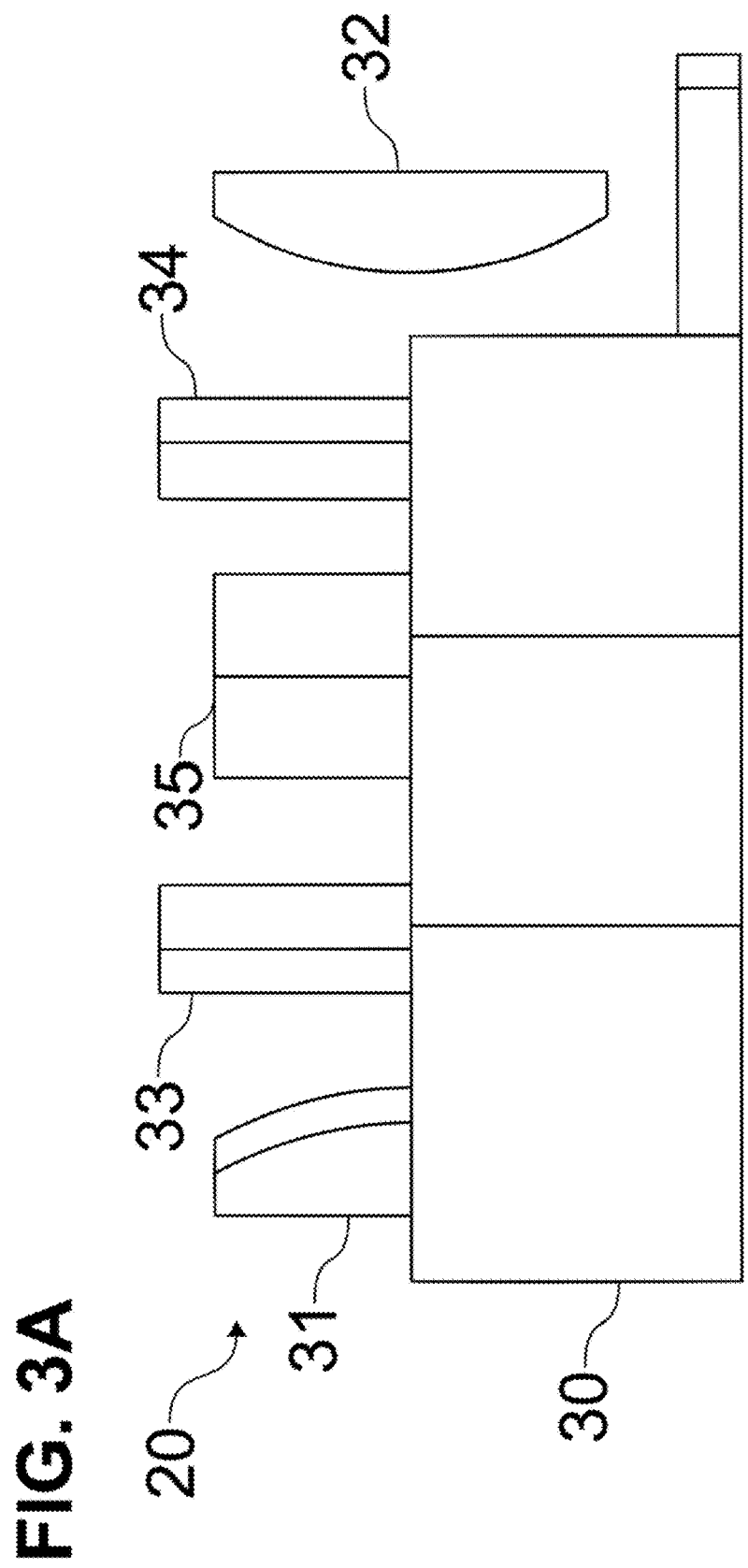
FIGS. 3A and 3B illustrate schematic side view and plan view, respectively, of an exemplary lens module in a steerable housing according to an embodiment.
Figure 3B:
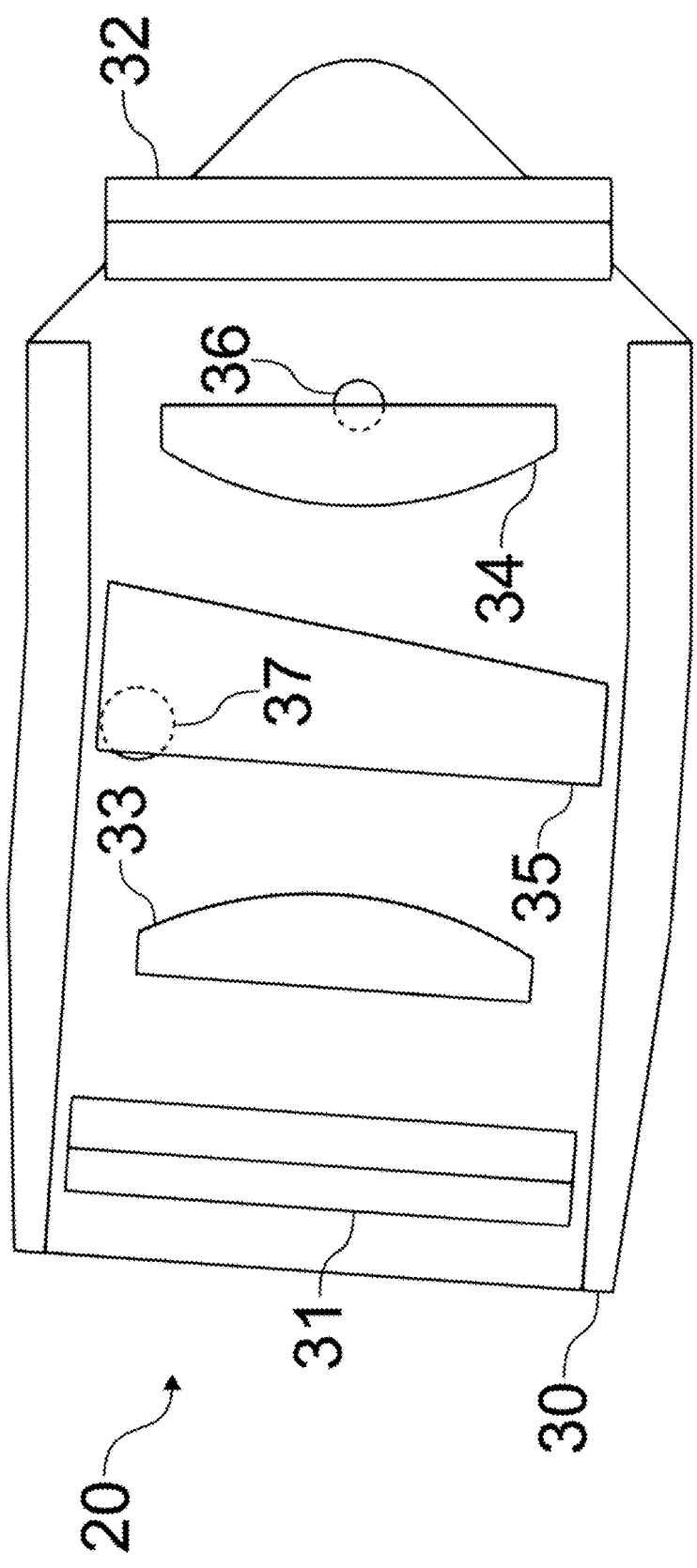

FIGS. 3A and 3B illustrate a side view and a plan view, respectively, of the lens module 20. The lens module 20 may include lenses mounted in a steerable lens housing 30. As used herein, a lens is any optical element having optical power, whether implemented by a refractive or diffractive element. Other elements not essential to understanding, such as a cover enclosing the lens module (see FIG. 2), are not shown for ease of illustration.

In the particular example shown herein, the lenses may include a pair of horizontal-axis cylindrical lenses 31-32 and a pair of vertical-axis cylindrical lenses 33-34. A prism element 35 is also shown which may align illumination light with the intended outgoing optical axis. In particular, the prism element 35 corrects for an angle introduced by the light pipe 21 for increased device compactness in accordance with an embodiment. The mounting design for each lens element 31-35 may allow for tuning of the magnification and focus of the illumination optical system. In accordance with this embodiment, the steerable lens housing 30 encloses and steers three of the cylindrical lenses 31, 33, 34 and the prism lens element 35, e.g., collectively as a group. This example of lenses is merely illustrative, and the lenses in the lens module 20 may be modified as appropriate.

In this particular embodiment, a base portion of the steerable housing 30 is pinned, e.g., using a pin 46 (see FIG. 6B) inserted into housing hole 37, about a pivot point 36, respectively to a fixed chassis frame 90 (see FIG. 6A) and a mechanical linkage 40 (see FIGS. 4A to 4C) described in detail below, while lens 32 is rigidly connected the chassis 90, i.e. not to the housing 30 (see FIG. 6B).

FIG. 4A illustrates a schematic view showing directions of motion provided by various components of the linkage 40. The linkage 40 may include a drive cam 41, illumination cams 45a, 45b (one for each illumination port), and an imaging cam 43. The drive cam 41 receives an input from a user (see FIG. 6), and translates that to synchronous motion of the lens module 20a, 20b, attached to a corresponding illumination cam 45a, 45b, via a respective housing 30 and a pin 46, and an imaging lens 51 and an imaging sensor 52 (see FIGS. 5A and 5B), attached to the imaging cam 43 via cam follower pins. Here, the imaging lens 51 is shown as a single field lens, but additional and/or alternative lenses for focusing light from the target 20 onto the imaging sensor 52 may be employed. Each port has its own associated illumination cam 45A and 45B, here shown as being to a left and right of an input window to receive light from the target 12.

In particular, translation of the drive cam 41 may translate the imaging cam 43 along the x-axis, which, in turn, may result in the imaging cam 43 to translate the imaging lens 51 and the imaging sensor 52 along the z-axis, as well as translate the illumination cams 45a, 45b, which, in turn, simultaneously steer corresponding lens modules 20a, 20b about respective pivot points 36, such that steering of the lens modules 20a, 20b is synchronously performed with the position adjustment of the imaging lens 51 and the imaging sensor 52 to insure proper focus of light from the target onto the sensor 52. Alternatively, the imaging cam 43 may translate only the imaging lens 51 along the z-axis, or any other combination of imaging optical elements in order to insure proper focus of light from the target onto the sensor 52.

FIG. 4B illustrates a bottom view and FIG. 4C illustrates a top view of the linkage 40 according to an embodiment. The drive cam 41 may include two drive parts 41a and 41b, and, if steering is included, a third drive part 41c, all of which are shown here as being rigidly attached to form a rigid drive cam 41. Similarly, the imaging cam 43 may include two imaging parts 43a and 43b. The drive cam 41 receives the input from a user (via control surface 62) via the first drive part 41a and translates the imaging cam 43 via a cam follower pin in drive part 41b, resulting in the imaging cam part 43a translating the sensor 52 and the imaging cam part 43b translating the imaging lens 51. If steering is included in the linkage, the third drive part 41c simultaneously steers (rotates) the lens modules 20a, 20b using the pin 46 (see FIG. 6B) associated with each of the illumination cam parts 45a and 45b, by translating the illumination cam parts 45a and 45b. The pin 46 may be inserted through a through a slot 49 in each of the illumination cams 45a, 45b and the corresponding housing hole 37 in the lens modules 20a, 20b. The drive part 41c steers the lens modules 20a, 20b simultaneously such that they both still illuminate a same field of view as one another at the target field of view of the target 12.

Figure 5A:
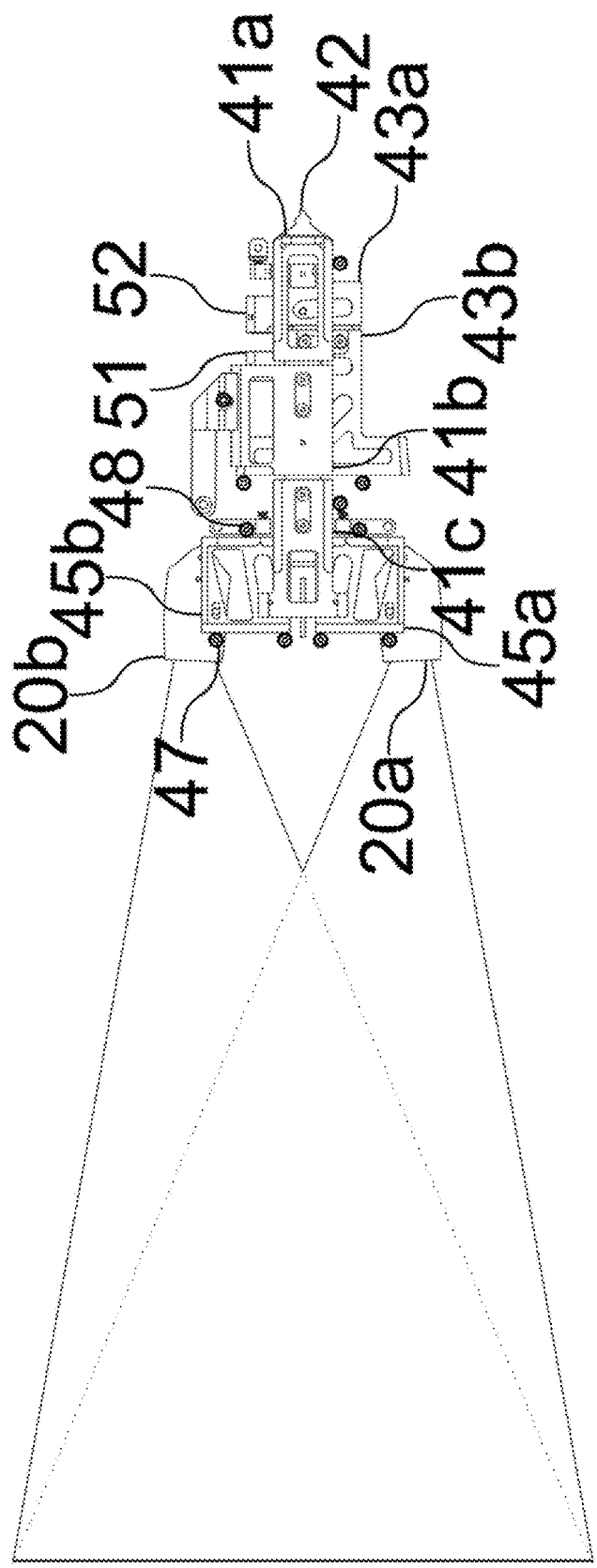
FIGS. 5A and 5B illustrate bottom views of the linkage at a far working distance and a near working distance, respectively, according to an embodiment.
Figure 5B:
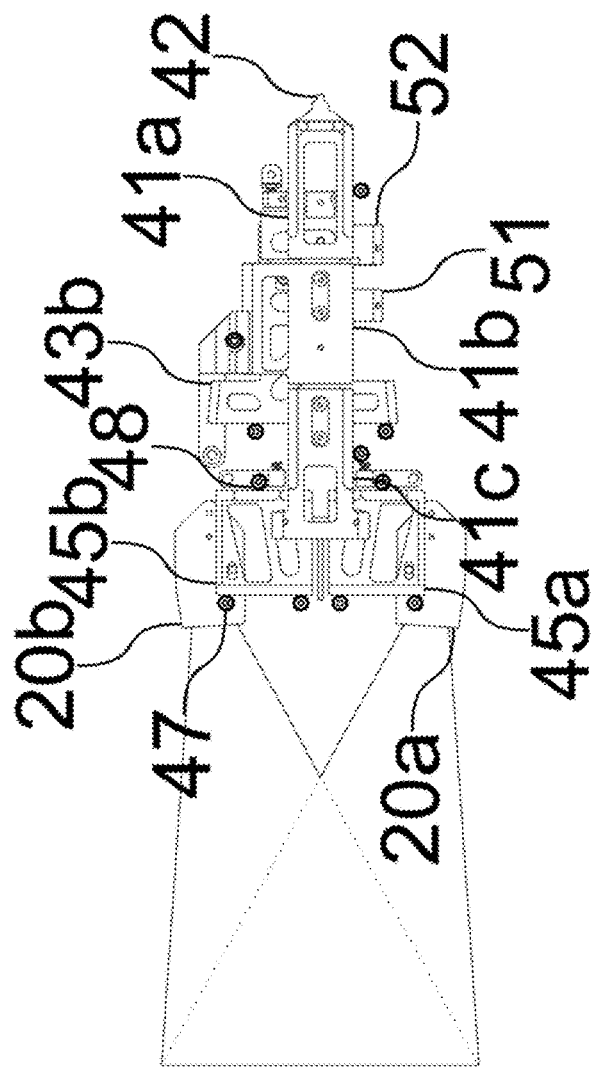

FIGS. 5A and 5B illustrate bottom views of the linkage combined with the lens modules 20a, 20b, the imaging field lens 51, and the sensor 52, at a far working distance and a near working distance, respectively, according to an embodiment. As can be seen therein, the linkage 40 synchronizes steering of the illumination sources with focusing of the imaging system at two sample working distance illumination steering settings. FIGS. 5A-5B show the positions of lens modules 20a, 20b (rotated about the pivot pint 37) and the lens 51 and sensor 52 (translated along an optical axis 55 of the imaging system and along the x-axis) at two focus positions resulting from user input.

As illustrated in FIGS. 5A and 5B, each part that moves axially within the linkage mechanism 40 may be guided by two fixed rolling elements 47, and one spring-loaded rolling element 48, in order to reduce or minimize friction during motion. The linkage 40 also may include a drive cam input connection point 42.

Figure 6B:
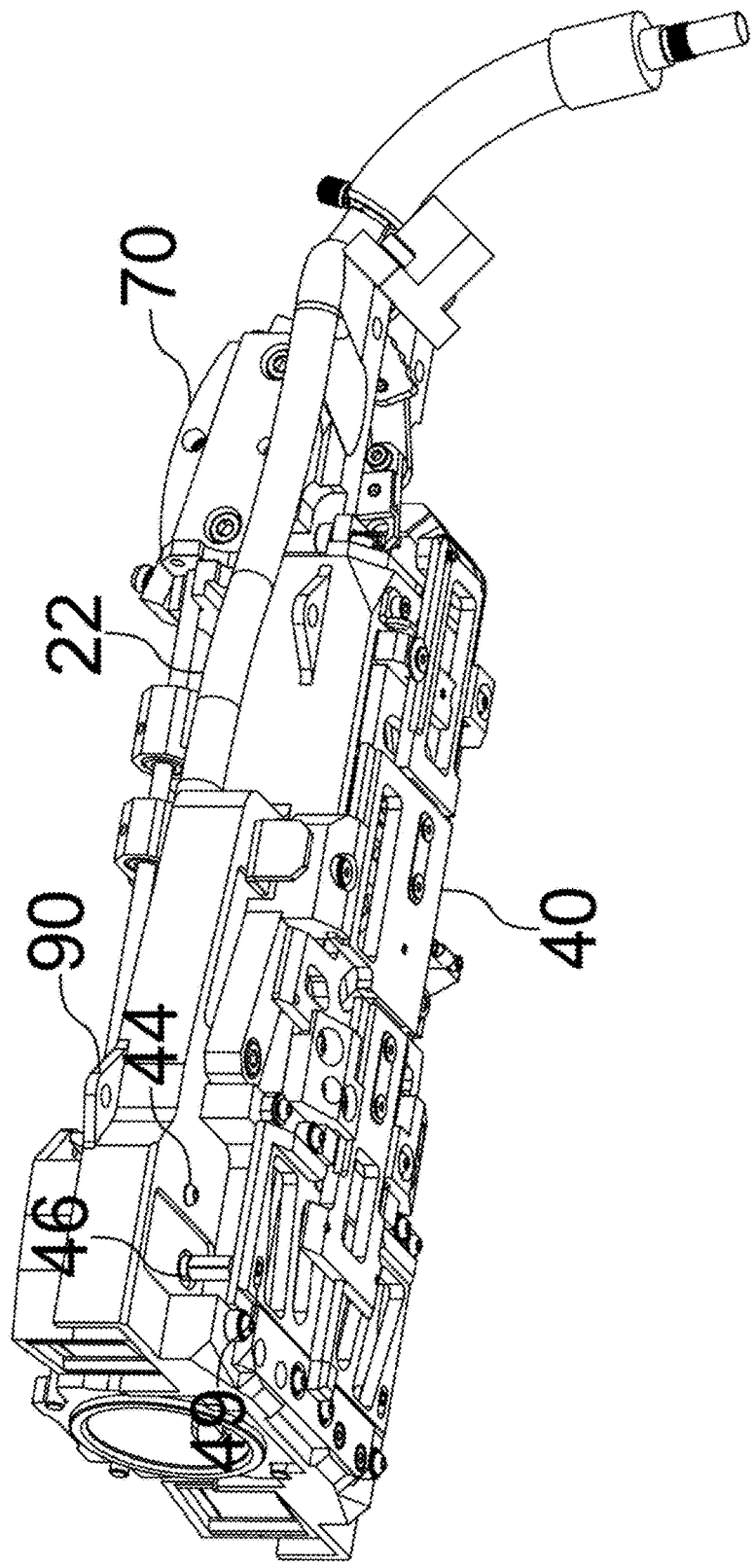

FIGS. 6A and 6B illustrate a perspective top view and a perspective bottom top view of the device 10 in accordance with an embodiment. In FIGS. 6A and 6B, the illumination module 11 and the imaging module 13 are mounted on the chassis 90, the top portion of which is removed in for clarity. Also, a focus actuation mechanism 70 is illustrated, which translates motion from user input to motion of the drive cam 41 via the drive cam input connection point 42.

As can be seen in FIG. 6A, an optical axis 55 of the imaging module 13 runs through a center of the imaging module, with the lens modules 20a, 20b being arranged symmetrically relative to the imaging optical axis 55. The light to be imaged from the target 12 travels along the optical axis 55 to be incident on the lens 51 and sensor 52. A wavelength-dependent aperture 53 that includes a smaller central aperture that permits transmission of all visible and fluoresced light, e.g., near infrared (NIR) light, and a surrounding larger aperture that blocks visible light but permits transmission of fluoresced light, may be provided upstream of the lens 51.

Referring to FIGS. 6B and 4A-4B, the pin 46 connects the lens module 20, via the housing hole 37 in the housing 30, slot 49 of the linkage 40. Also, a pivot point pin 44 connects the lens module 20 to the chassis 90.

Figure 7:
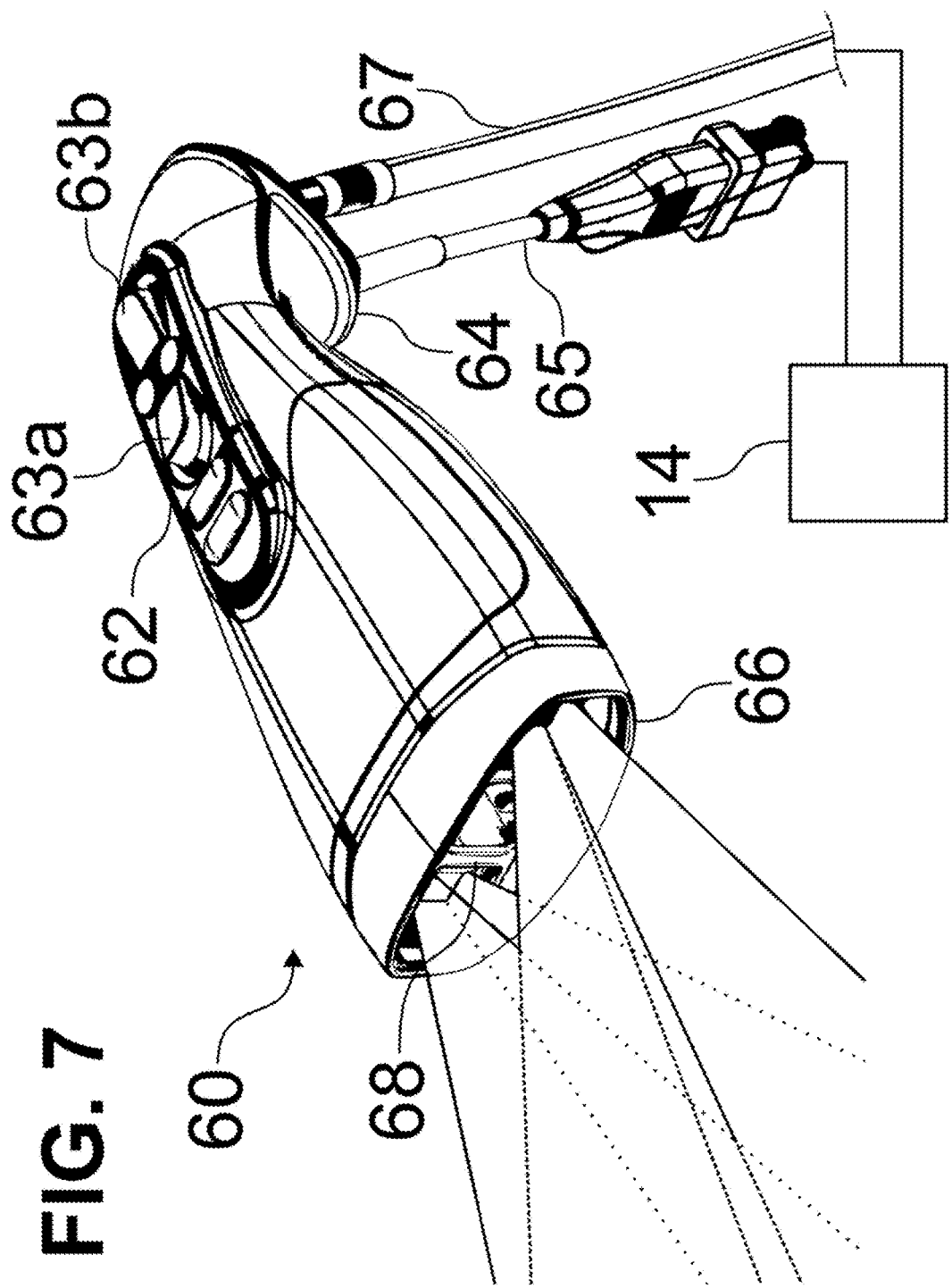
FIG. 7 illustrates an enclosure according to an embodiment.
Figure 8B:
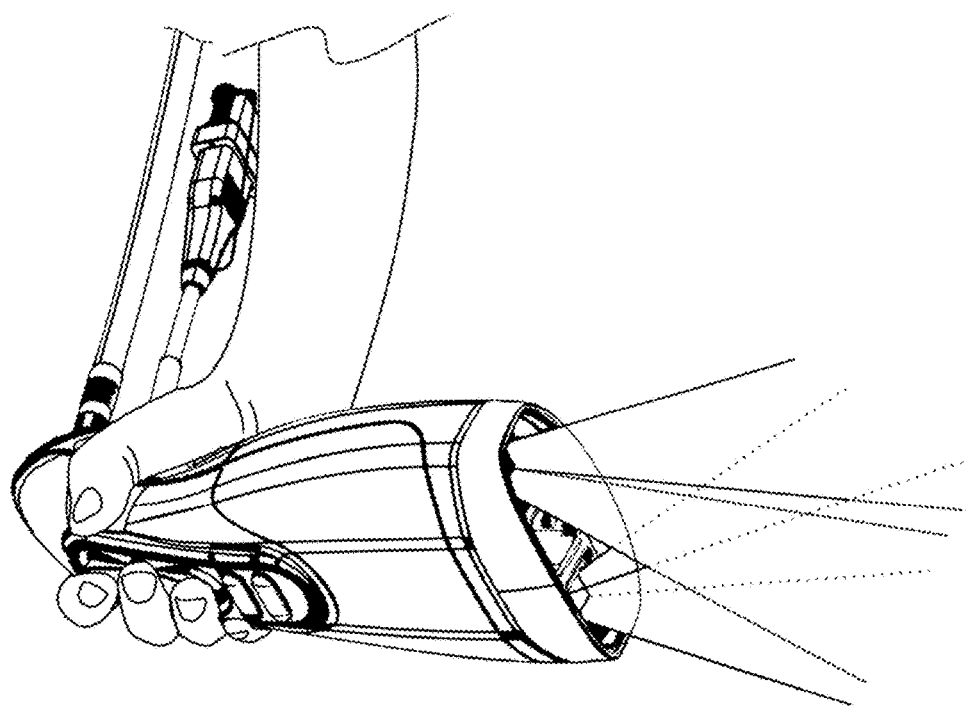

FIG. 7 illustrates an embodiment of an ergonomic enclosure 60 enclosing the illumination module 11 and the imaging module 13. The ergonomic enclosure 60 is designed to be held in different use-modes/configurations, for example, a pistol-style grip for forward imaging in a scanning-imaging orientation (FIG. 8A), and a vertical-orientation grip for use when imaging downward in an overhead imaging orientation (FIG. 8B). As may be seen in FIG. 7, the enclosure 60 includes a control surface 62, a grip detail 64, a window frame 68 and a nosepiece 66. The ergonomic enclosure 60 is connectable to the VPI box 14 via a light guide cable 67, through which the light is provided to the illumination ports 20a, 20b, and a data cable 65 that transmits power, sensor data, and any other (non-light) connections.

The control surface 62 includes focus buttons 63a (decreasing the working distance) and 63b (increasing the working distance) that control the linkage 40. Other buttons on the control surface 62 may be programmable and may be used for various other functions, e.g., excitation laser power on/off, display mode selection, white light imaging white balance, saving a screenshot, and so forth. Alternatively or additionally to the focus buttons, a proximity sensor may be provided on the enclosure and may be employed to automatically adjust the linkage 40.

As can be seen in FIG. 8A, when the enclosure 60 is held with the imaging window facing forward, the thumb rests on the control surface 62 while the other fingers on the operator's hand are wrapped loosely around the bottom of the grip detail 64. As can be seen in FIG. 8B, when the enclosure 60 is held with the imaging window facing downward, the grip detail 64 is between the thumb and index finger and the fingers are wrapped around to access the control buttons or switches on the control surface 62. The grip detail 64 is sculpted so as to provide for partial support of the device weight on the top of the wrist in the vertical-orientation grip, such that the enclosure 60 can hang loosely and without the need for a tight grip of the enclosure 60. Thus, the enclosure 60 may be operated by a single hand in multiple orientations. In various other embodiments, the enclosure 60 may be supported on a support (e.g., a moveable support).

The window frame 68 (see also FIG. 9), defines the different windows for the enclosure 60. In other words, the window frame 68 defines windows 68a and 68b, corresponding to the two lens modules 20a and 20b, as well as window 68c, which serves as an input window for light from the target to be incident on the sensor 52.

Figure 9:
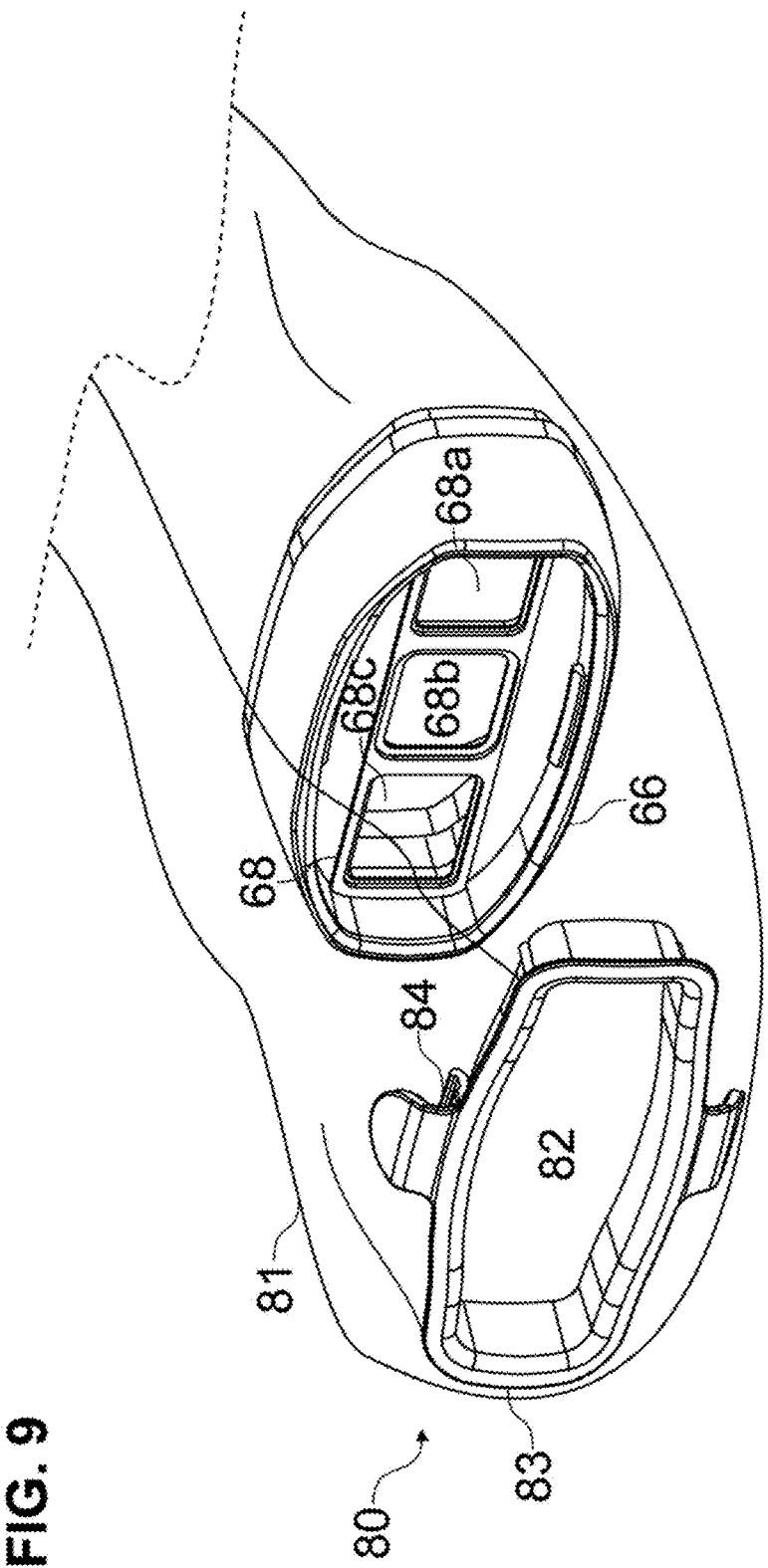
FIG. 9 illustrates a drape for use with the system according to an embodiment.

As illustrated in FIG. 9, the enclosure 60 may be used in concert with a drape 80. The drape 80 may be a surgical drape suitable for use during a surgical procedure. The drape includes drape material 81, a drape lens 82, a drape window frame 83 surrounding the drape lens, and an interlock interface 84 that is integral with the drape window frame 83. The drape material 81 is to envelope the device in the enclosure 60, as well as to cover anything else as required. The drape window frame 83 may follow a shape of the enclosure nosepiece 66 such that the drape window frame 83 may be inserted therein without obstructing the windows 68a to 68c. The drape 80 is designed to minimize reflections and imaging ghosting by ensuring the drape lens 82 is flush, e.g., to within 0.5 mm, with the imaging and illumination window frame 68. The drape 80 may use the interlock interface 84, which may fit into a recess on the inner surface of the enclosure nosepiece 66, to be secured flush thereto.

One or more interlock interfaces 84 may be used on the inner or outer surface of the enclosure nosepiece 66, in order to ensure a secure and close fit of the drape lens 82 against the window frame 68. In the particular embodiment shown, two interfaces 84, here one on the top and one on the bottom of the drape window frame 83 to engage with an inner surface of the enclosure nosepiece 66, are used.

Figure 10B:
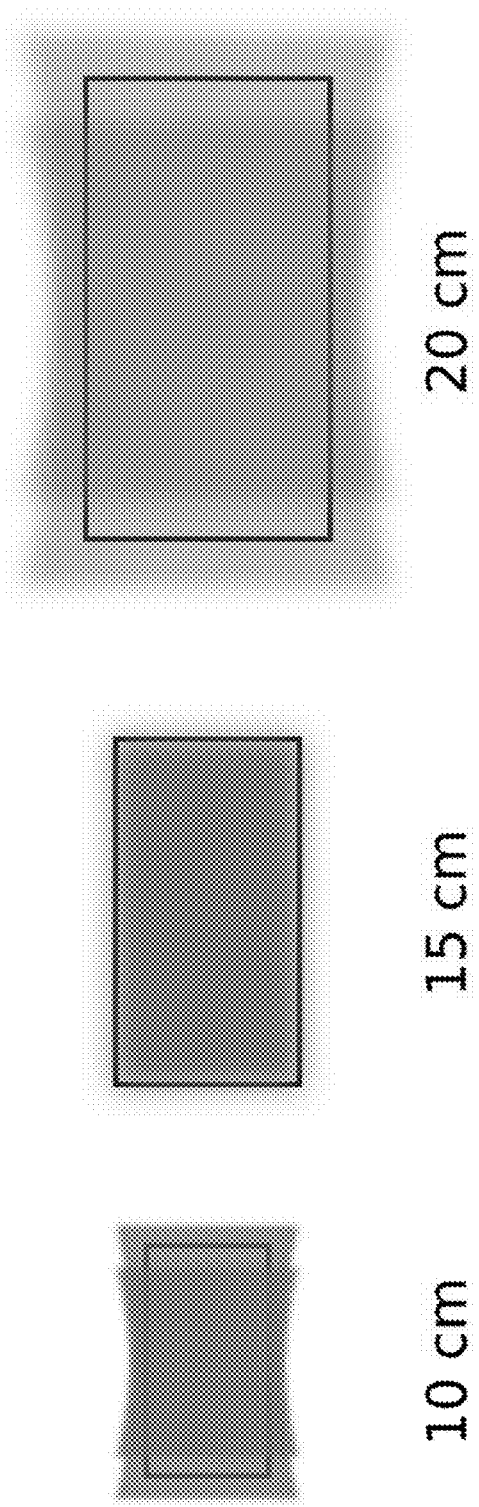

FIGS. 10A to 10C illustrate typical illumination distributions (fill) relative to a rectangular imaging field of view (outline) for an illumination ring (FIG. 10A), a pair of fixed anamorphic projection illumination sources (FIG. 10B), and a pair of steered anamorphic projection illumination sources in accordance with an embodiment (FIG. 10C) at working distances of 10 cm (left column), 15 cm (center column), and 20 cm (right column). FIG. 10A illustrates use of a ring of illumination ports to minimize shadowing, but does not match illumination to the imaging field of view and may not provide even illumination at all working distances (e.g. varied distributions in accordance with distance). FIG. 10B illustrates anamorphic projection from two illumination sources (using, e.g., an illumination lens arrangement featuring cylindrical lenses or an engineered diffuser) that are fixed, thus they are well calibrated for even illumination that matches the imaging field of view at a fixed working distance, e.g., 15 cm, but not as even or well matched at other distances, whether smaller or greater. As noted above, such illumination is often acceptable on its own. FIG. 10C illustrates the ability to better maintain even illumination and constrain illumination to the field of view by steering illumination when changing the working distance (and imaging focus) in accordance with an embodiment.

As noted above, the illumination used may include both white light and fluorescence excitation illumination, e.g., from a laser, to excite near infrared (NIR) light from the target. However, ambient light may interfere with the light from the target.

FIG. 11A illustrates a timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor. As used herein, a white pulse will indicate that the white light (RGB) is illuminating the target and an excitation pulse will indicate that the laser is illuminating the target.

Exposures of even (Exp 1) and odd (Exp 2) sensor pixel rows are shown interleaved with differing exposure times to facilitate isolation of an estimate of the ambient room light signal component. Such an interleaved exposure read-out mode is offered on some imaging sensors, such as the 'High Dynamic Range Interleaved Read-out' mode offered on the CMOSIS CMV2000 sensor.

Pulsing the white light illumination at 80 Hz brings the frequency of the flashing light above that which is perceptible by the human eye or which may trigger epileptic seizures. The visible light image exposure may be longer than, e.g., twice, the RGB illumination to ensure overlap between the 60 Hz exposure frame rate and the 80 Hz RGB illumination pulse. Extra ambient light captured during the visible exposure may be ignored, due to the much greater intensity of the RGB illumination pulse and signal from the target 12.

By setting the NIR fluorescence image exposure times Exp 1 and Exp 2 to acquire for one half frame and one quarter frame periods, respectively, while running the excitation laser only in the last one quarter of every third frame, the even rows (Exp 1) record one half frame of ambient room light in addition to one quarter frame of NIR fluorescence, while the odd rows (Exp 2) record one quarter frame of ambient room light plus one quarter frame of NIR fluorescence. Performing these fractional exposures within each visible or NIR fluorescence frame minimizes motion artifacts which would otherwise be caused by inserting additional exposure frames into the frame sequence for the purpose of ambient room light subtraction.

With such an acquisition design, an estimate of the ambient room light contribution to the image signals can be isolated by subtracting the Exp 2 sensor rows of the NIR fluorescence image from the Exp 1 sensor rows (interpolated to match Exp 2 pixel positions), yielding an estimate of one quarter frame of ambient room light signal. The estimate of one quarter frame of ambient room light signal can then be subtracted from the Exp 2 sensor rows of the NIR fluorescence image to yield an estimate of the NIR fluorescence signal with the one quarter frame of ambient room light removed. The control of the illumination and the exposure may be performed by the VPI box 14.

Figures 12A, 12B, 12C:
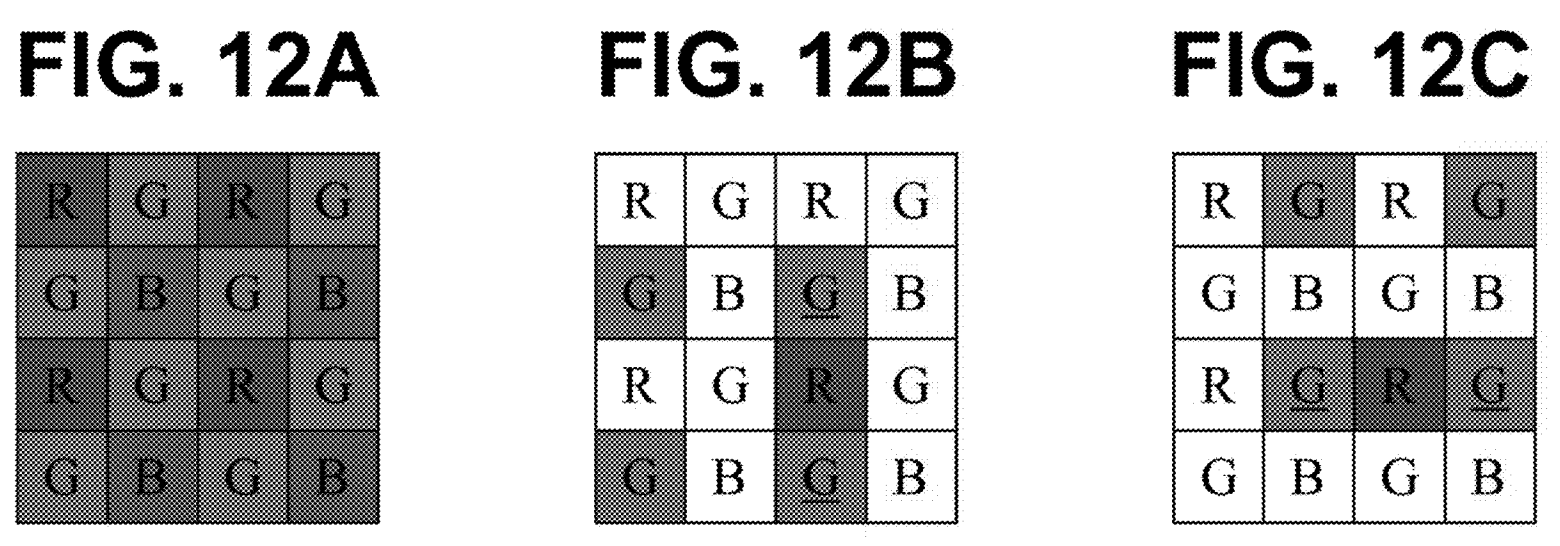

In one embodiment, the above room light subtraction method may be altered in order to accommodate use of a Bayer-pattern color sensor. FIG. 12A illustrates a Bayer pattern arrangement of colored sensor pixels, wherein the even sensor rows and odd sensor rows have different filter arrangements (e.g., no red pixels in the even sensor rows and no blue pixels in the odd sensor rows), so the ambient light recorded on even rows will not be a good estimate of what reached the odd rows over the same period. However, every row does include green pixel signals, which are also sensitive to NIR fluorescence. Using only the green pixels, and performing a two-dimensional interpolation from the green pixel signals to the other pixel locations can yield an estimate of the ambient light signal component, and thus also of the NIR fluorescence or visible light components for the NIR and visible light images, respectively.

In order to calculate the NIR signal value at a given location, calculate the Exp 1 (even row) and Exp 2 (odd row) green pixel values near that location, with one or both of those values needing to be interpolated. FIG. 12B demonstrates an example wherein at a red pixel location, the best estimate of the Exp 1 (even row) green value is the average of the immediately neighboring green values above and below, while the best estimate of the Exp 2 (odd row) green value is the average of the immediately neighboring green values to the left and right.

The following mathematical example serves to illustrate an embodiment of the ambient room light subtraction method. If A=ambient light incident in one quarter frame period, and F=fluorescence incident in one quarter frame period, then:

$$Exp\ 1=2A+F$$

$$Exp\ 2=A+F$$

Solving for F yields:

$$F=2*Exp2-Exp1$$

In the particular example illustrated in FIG. 11A, a period for the sensing is three frames, the white light pulse and the excitation pulse have a same duration or width, but different frequencies, the visible light is sensed during two frames, e.g., the first two frames, and the fluorescence is sensed for during one frame, e.g., the third or final frame, for two different exposure times. As shown therein, the visible exposure time may be twice the duration of the white light pulse, a first fluorescent exposure times may be equal to the duration of the excitation pulse, and a second fluorescent exposure time may be pulse longer, e.g., twice, than the excitation pulse. Further, the visible exposure may have a different frequency than the white light pulse, e.g., visible exposure does not occur with every white light pulse, while the fluorescent exposure may have a same frequency as the excitation pulse.

Alternative timing and exposure diagrams are discussed below, in which a sensor having rows that are all active for a common exposure duration may be used while still compensating for ambient light using a single sensor. For example, background light may be directly detected by the sensor when the target is not illuminated. Other variations on pulsing, exposing, and sensing may be apparent to those of skill in the art.

FIG. 11B illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor. Exposures for visible light and for fluorescence are shown in sequence along with an exposure to capture the background (BG) image signal due to ambient light. The white light illumination may be pulsed at 80 Hz as described above. The fluorescence excitation illumination may be pulsed at 20 Hz and the pulse duration or width may be increased, e.g., up to double the white light pulse duration, to enable a longer corresponding fluorescence exposure. If using an imaging sensor with a global shutter, each sensor exposure must terminate with the read-out period at the end of an imaging frame. An exposure to capture the ambient light background image signal may be performed at the end portion of a frame in the absence of any pulsed white light or excitation light. In the case of acquiring video at a frame rate of 60 Hz, as shown in the example in FIG. 11B, a white light illumination pulse width of one quarter frame duration may be used, along with a one quarter frame duration visible light exposure occurring in frames when the end of a white light illumination pulse is aligned with the end of the frame.

A scaled image signal recorded during one or more background exposures can be subtracted from each fluorescence exposure image to remove the contribution of ambient light from the fluorescence image. For example, the image signal from a one quarter frame duration background exposure may be scaled up by two times and subtracted from a subsequent image signal from a one half frame duration fluorescence exposure. As another example, a one quarter frame duration background exposure image signal prior to a one half frame duration fluorescence exposure image signal, and a second one quarter frame background image signal subsequent to the fluorescence exposure, may both be subtracted from the fluorescence image signal. Scaling of the image signals from a first and a second background exposure can include interpolation of pixel values from the first exposure time point and the second exposure time point to estimate pixel values corresponding to an intermediate time point.

Use of an imaging sensor with high speed read-out that enables higher video frame acquisition rates may allow for additional exposure periods to be allocated within an illumination and exposure timing scheme for a given white light pulse frequency. For example, maintaining an 80 Hz white light illumination pulse as above and using a sensor with a higher video frame acquisition rate such as 120 Hz may allow additional white light, ambient background, or fluorescence exposures within a given time period, compared to when using a slower video frame acquisition rate such as 60 Hz.

In the particular example illustrated in FIG. 11B, a period for the sensing is three frames, the excitation pulse has twice the width of the white light pulse, the visible light is sensed during one frame, e.g., the first frame, the background light is sensed during one frame, e.g., the second frame, and the fluorescence is sensed during one frame, e.g., the third or final frame. Here, a visible exposure time may be equal to the duration of the white light pulse, the background exposure time may be equal to the duration of the white light pulse, and the fluorescence exposure time may be equal to the duration of the excitation pulse. Further, the visible exposure may have a different frequency than the white light pulse, e.g., visible exposure does not occur with every white light pulse, while the fluorescent exposure may have a same frequency as the excitation pulse. Finally, the background exposure may occur only once within the period.

FIG. 11C illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor with a 120 Hz video frame acquisition rate. A white light pulse frequency of 80 Hz is used, and a white light illumination pulse width of one half frame duration may be used, along with a one half frame duration visible light exposure occurring in frames when the end of a white light illumination pulse is aligned with the end of the frame. The fluorescence excitation illumination is shown pulsed at 40 Hz with a pulse duration of one frame, to enable a higher frequency of corresponding fluorescence exposures. An exposure to capture the ambient light background image signal may be performed at the end portion of a frame in the absence of any pulsed white light or excitation light, such as an exposure of one half frame duration occurring in the frame between a fluorescence exposure and a successive white light exposure as shown in this example embodiment.

In the particular example illustrated in FIG. 11C, a period for the sensing is three frames, the excitation pulse has twice the width of the white light pulse, the visible light is sensed during one frame, e.g., the second frame, the background light is sensed during one frame, e.g., the first frame, and the fluorescence is sensed during one frame, e.g., the third or final frame. Here, a visible exposure time may be equal to the duration of the white light pulse, the background exposure time may be equal to the duration of the white light pulse, and the fluorescence exposure time may be equal to the duration of the excitation pulse. Further, the visible exposure may have a different frequency than the white light pulse, e.g., visible exposure does not occur with every white light pulse, while the fluorescent exposure may have a same frequency as the excitation pulse. Finally, the background exposure may occur only once within the period.

Depending on the intensity of the fluorescence excitation light used, there may be safety considerations limiting the duration and frequency of excitation light pulses. One approach to reduce the excitation light intensity applied is to reduce the duration of the excitation light pulses and the corresponding fluorescence exposures. Additionally or alternatively, the frequency of excitation light pulses (and corresponding fluorescence exposures) may be reduced, and the read-out periods which could otherwise be used for fluorescence exposures may instead be used for background exposures to improve measurement of the ambient light.

FIG. 11D illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor with a 120 Hz video frame acquisition rate. A white light pulse frequency of 80 Hz is used, and a white light illumination pulse width of one half frame duration may be used, along with a one half frame duration visible light exposure occurring in frames when the end of a white light illumination pulse is aligned with the end of the frame. The fluorescence excitation illumination is shown pulsed at 20 Hz with a pulse duration of one frame. An exposure to capture the ambient light background image signal may be performed at the end portion of a frame in the absence of any pulsed white light or excitation light, such as a background exposure of one half frame duration occurring in the frame between a fluorescence exposure and a successive first white light exposure, and a first background exposure of one frame duration and a second background exposure of one half frame duration both occurring in the frames between the first white light exposure and a successive second white light exposure, as shown in this example embodiment.

In the particular example illustrated in FIG. 11D, a period for the sensing is six frames, the excitation pulse has twice the width of the white light pulse, the visible light is sensed during two frames, e.g., the second and fifth frames, the background light is sensed during three frames, e.g., the first, third, and fourth frames, and the fluorescence is sensed for during one frame, e.g., the sixth or final frame. Here, a visible exposure time may be equal to the duration of the white light pulse, the background exposure time may be equal to or twice the duration of the white light pulse, and the fluorescence exposure time may be equal to the duration of the excitation pulse. Further, the visible exposure may have a different frequency than the white light pulse, e.g., visible exposure does not occur with every white light pulse, e.g., only twice within the period, while the fluorescent exposure may have a same frequency as the excitation pulse. Finally, the background exposure may occur three times within the period for a total duration equal to four times the duration of the white light pulse.

To improve performance of such ambient room light compensation methods as described above, a wavelength-dependent aperture (e.g., element 55 in FIG. 6A) may be used that includes a smaller central aperture that permits transmission of all visible and NIR light, and a surrounding larger aperture that blocks visible light but permits transmission of NIR light. Use of such a wavelength-dependent aperture allows a larger proportion of NIR signal to be collected relative to the visible light signal, which improves performance of the image signal subtraction for estimation and removal of the ambient room light component. A wavelength-dependent aperture may also feature a third, larger aperture, surrounding the other smaller apertures, that blocks both visible and NIR light. As an example, a wavelength-dependent aperture may comprise a film aperture, wherein a film (e.g., a plastic or glass film) of material that blocks transmission of visible light but permits transmission of NIR light has a central opening (e.g., a hole) that permits transmission of both visible and NIR light. Such a film aperture may comprise material that blocks transmission of visible light through reflection and/or material that blocks transmission of visible light through absorption. As another example, a wavelength-dependent aperture may comprise a dichroic aperture which is formed by masked thin-film deposition on a single substrate, wherein a thin-film that permits transmission of visible and NIR light is deposited on a smaller central aperture, and a second thin-film that blocks transmission of visible light but permits transmission of NIR light is deposited on a surrounding larger aperture. The respective aperture sizes of the smaller central aperture and the surrounding larger aperture of a wavelength-dependent aperture may be set in order to make the depth of field for visible light and for NIR light appear substantially similar when imaged by the imaging system. One or more wavelength-dependent filters may be placed in different positions throughout the device, where rejection of the visible and passage of the NIR signal may be optimized. For example, such a wavelength-dependent filter may be positioned just before the lens 51. As another example, one or more wavelength-dependent filters may be placed in a pupil plane of the imaging lens.

It may be useful, e.g., to facilitate comparison of the fluorescence signal of different regions, to display a target reticle around a region within the imaged field of view, and to calculate and display the normalized fluorescence intensity within that region. Normalization of the measured fluorescence intensity values may allow for meaningful comparison of multiple images and corresponding values. To correct for the variation of measured fluorescence intensity with working distance (e.g., distance of the imaging system to the imaged anatomy), normalized fluorescence intensity values may be based on a ratio between the measured fluorescence intensity values and a reflected light value within the target reticle region.

A numerical representation of the normalized fluorescence intensity value within the target reticle region may be displayed on or near the image frame, to facilitate comparing values when aiming the target reticle at different locations on the imaged anatomy. For example, the numerical representation may be the mean value of the normalized fluorescence intensity values for all of the image pixels in the target reticle region.

Additionally or alternatively, a time history plot of the numerical representation of the normalized fluorescence intensity value within the target reticle region may be displayed on or near the image frame, to facilitate comparing values when aiming the target reticle at different locations on the imaged anatomy or at the same location over a series of time points. Such a time history plot may further assist the user in assessing the fluorescence profile in the imaged tissue surface by scanning across the anatomy region of interest and viewing the relative normalized fluorescence intensity profile plot.

Figure 13A:
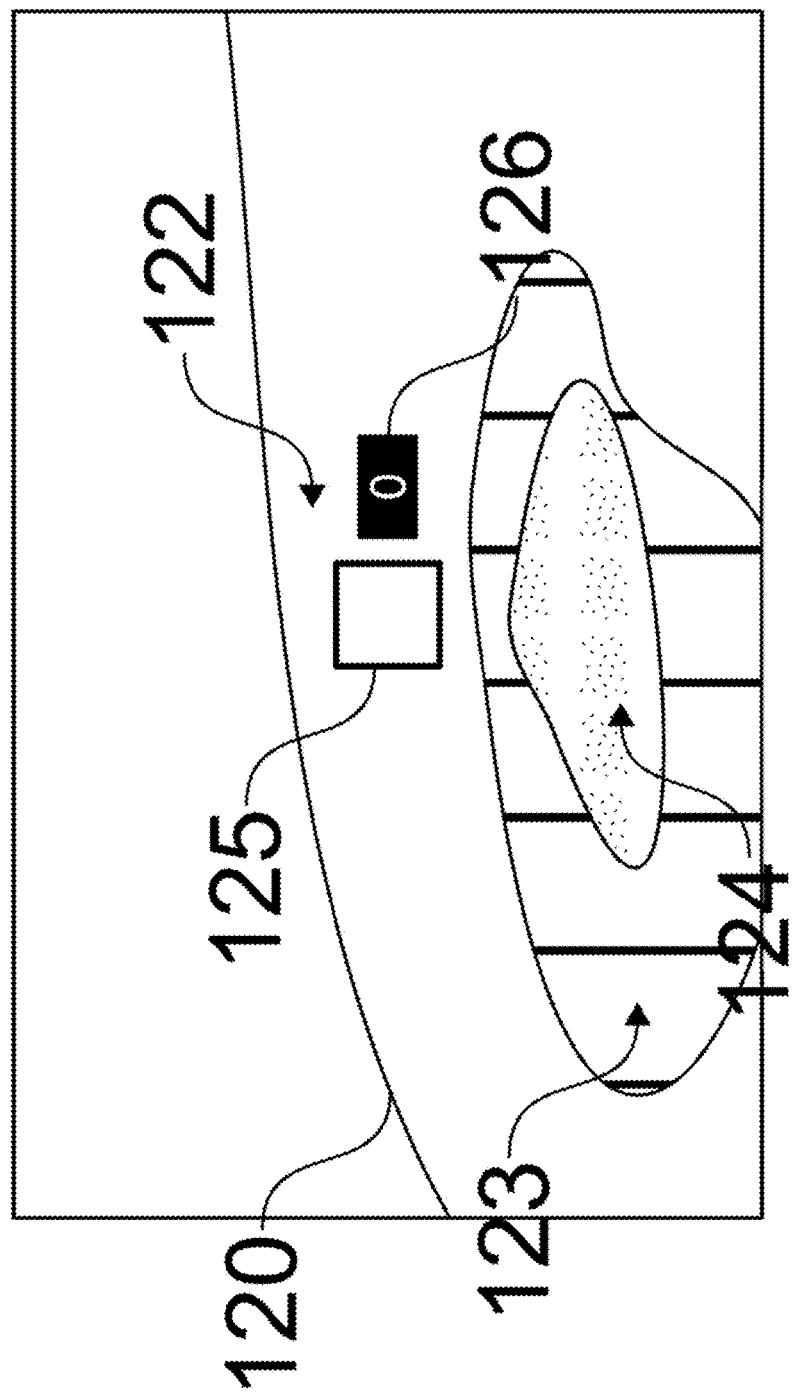
Figure 13D:
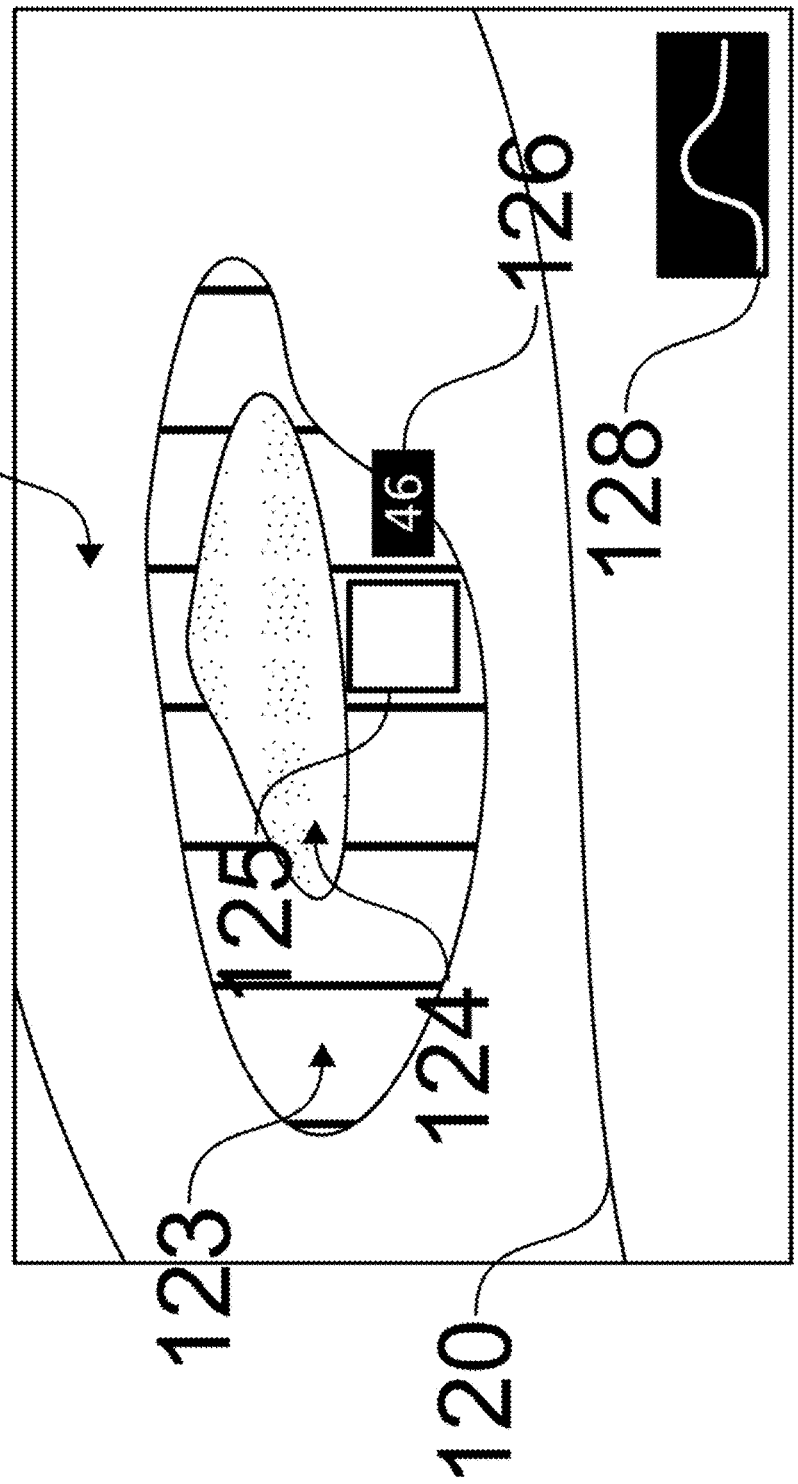
FIG. 13D illustrates a diagram of an embodiment of a display method output that includes a signal time history plot of normalized fluorescence intensity values on the display.

FIG. 13A illustrates a diagram of a sample display output from an embodiment of the display method, wherein the target reticle 125 is positioned over a region of no fluorescence intensity 122 on the imaged anatomy 120, and the numerical representation of the fluorescence intensity 126 is displayed near the target reticle 125. FIG. 13B illustrates a diagram of another sample display output, wherein the target reticle 125 is positioned over a region of high relative normalized fluorescence intensity 124, and showing a corresponding numerical representation 126 of relatively high fluorescence intensity. FIG. 13C illustrates a diagram of another sample display output, wherein the target reticle 125 is positioned over a region of moderate relative normalized fluorescence intensity 124, and showing a corresponding numerical representation 126 of relatively moderate fluorescence intensity. FIG. 13D illustrates a diagram of a sample display output, wherein the target reticle 125 is positioned over a region of moderate relative normalized fluorescence intensity 124, and showing a time history plot 128 of the numerical representation of normalized fluorescence intensity that would be consistent with sequential imaging of regions of zero, high, and moderate relative normalized fluorescence intensity. Alternatively or additionally to displaying the numerical representation and/or historical plot on the target, a display region associated with the target reticle, e.g., on the device itself or some other display, may display this information.

Figure 14:
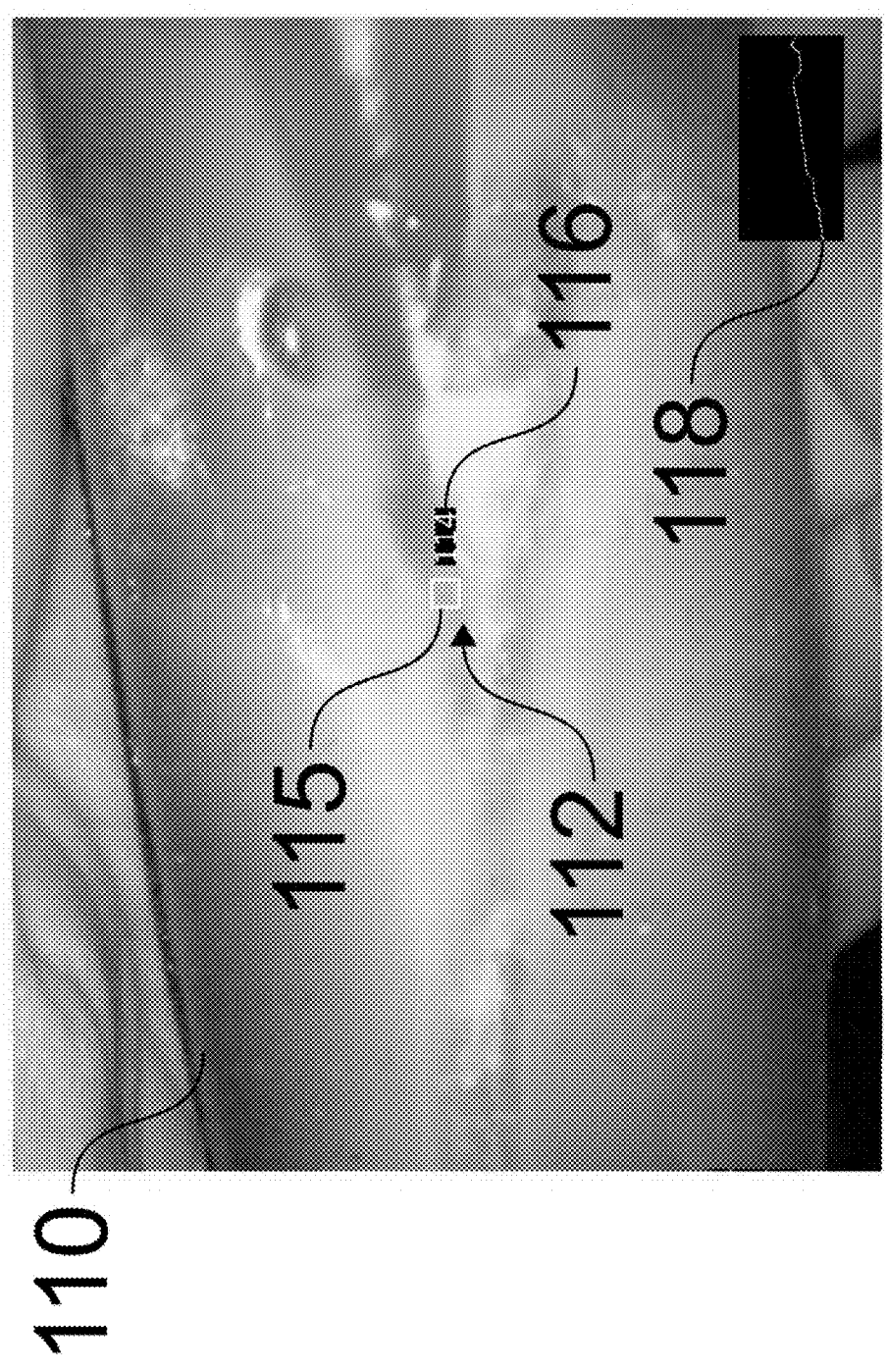
FIG. 14 illustrates a recorded image of an anatomical fluorescence imaging phantom, featuring an embodiment of a display method output that displays normalized fluorescence intensity.

FIG. 14 illustrates a recorded image of an anatomical fluorescence imaging phantom, featuring an embodiment of a display method output that displays normalized fluorescence intensity. In particular, a target 110 is illuminated by excitation light in accordance with an embodiment and a target reticle 115 is positioned over a region of fluorescence intensity 112. A numerical representation of the target reticle 115 is displayed in a region 116 associated with the target reticle 115. A time history plot 118 of the numerical representation of normalized fluorescence intensity due to imaging of different positions of the reticle 115 may be displayed.

Such a display method may be useful for a variety of fluorescence imaging systems, including an endoscopic or laparoscopic fluorescence imaging system, an open field fluorescence imaging system, or a combination thereof. Such normalization and display of the fluorescence intensity values can allow useful quantitative comparisons of relative fluorescence intensity between image data from various time points within an imaging session. Combined with appropriate standardized fluorescent agent administration and imaging protocols, and standardized calibration of imaging devices, such normalization and display of the fluorescence intensity values can further allow useful quantitative comparisons of relative fluorescence intensity between image data from different imaging sessions.

EXAMPLES

A Fluorescence Medical Imaging System for Acquisition of Image Data

In some embodiments, a system for illumination and imaging of a subject may be used with or as a component of a medical imaging system such as, for example, a fluorescence medical imaging system for acquiring fluorescence medical image data. An example of such a fluorescence medical imaging system is the fluorescence imaging system 10 schematically illustrated in FIG. 1. In this embodiment, the fluorescence imaging system 10 is configured to acquire a time series of fluorescence signal intensity data (e.g., images, video) capturing the transit of a fluorescence imaging agent through the tissue.

The fluorescence imaging system 10 (FIG. 1) comprises an illumination source 15 and illumination module 11 to illuminate the tissue of the subject to induce fluorescence emission from a fluorescence imaging agent 17 in the tissue of the subject (e.g., in blood), an imaging module 13 configured to acquire the time series of fluorescence images from the fluorescence emission, and a processor assembly 16 configured to utilize the acquired time series of fluorescence images (fluorescence signal intensity data) according to the various embodiments described herein.

In various embodiments, the illumination source 15 (FIG. 1) comprises, for example, a light source 200 (FIG. 15) comprising a fluorescence excitation source configured to generate an excitation light having a suitable intensity and a suitable wavelength for exciting the fluorescence imaging agent 17. The light source 200 in FIG. 15 comprises a laser diode 202 (e.g., which may comprise, for example, one or more fiber-coupled diode lasers) configured to provide excitation light to excite the fluorescence imaging agent 17 (not shown). Examples of other sources of the excitation light which may be used in various embodiments include one or more LEDs, arc lamps, or other illuminant technologies of sufficient intensity and appropriate wavelength to excite the fluorescence imaging agent 17 in the tissue (e.g., in blood). For example, excitation of the fluorescence imaging agent 17 in blood, wherein the fluorescence imaging agent 17 is a fluorescent dye with near infra-red excitation characteristics, may be performed using one or more 793 nm, conduction-cooled, single bar, fiber-coupled laser diode modules from DILAS Diode Laser Co, Germany.

Figure 15:
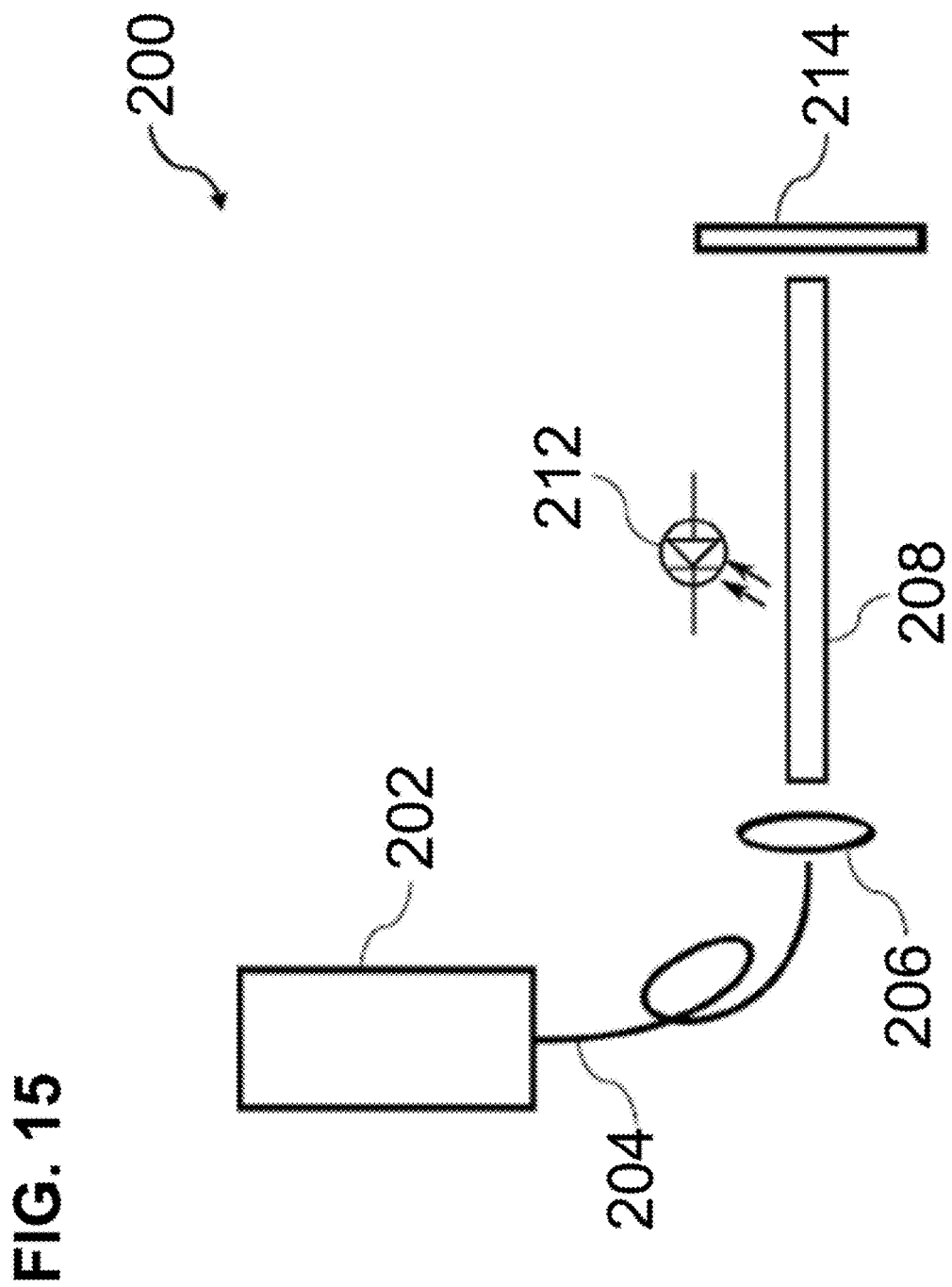
FIG. 15 illustrates an exemplary light source of an exemplary illumination source of the system for illumination shown in FIG. 1.

In various embodiments, the light output from the light source 200 in FIG. 15 may be projected through an optical element (e.g., one or more optical elements) to shape and guide the output being used to illuminate the tissue area of interest. The shaping optics may consist of one or more lenses, light guides, and/or diffractive elements so as to ensure a flat field over substantially the entire field of view of the imaging module 13. In particular embodiments, the fluorescence excitation source is selected to emit at a wavelength close to the absorption maximum of the fluorescence imaging agent 17 (e.g., ICG). For example, referring to the embodiment of the light source 200 in FIG. 15, the output 204 from the laser diode 202 is passed through one or more focusing lenses 206, and then through a homogenizing light pipe 208 such as, for example, light pipes commonly available from Newport Corporation, USA. Finally, the light is passed through an optical diffractive element 214 (e.g., one or more optical diffusers) such as, for example, ground glass diffractive elements also available from Newport Corporation, USA. Power to the laser diode 202 itself is provided by, for example, a high-current laser driver such as those available from Lumina Power Inc. USA. The laser may optionally be operated in a pulsed mode during the image acquisition process. In this embodiment, an optical sensor such as a solid state photodiode 212 is incorporated into the light source 200 and samples the illumination intensity produced by the light source 200 via scattered or diffuse reflections from the various optical elements. In various embodiments, additional illumination sources may be used to provide guidance when aligning and positioning the module over the area of interest. In various embodiments, at least one of the components of light source 200 depicted in FIG. 15 may be components comprising the illumination source 15 and/or comprising the illumination module 11.

Figure 16:
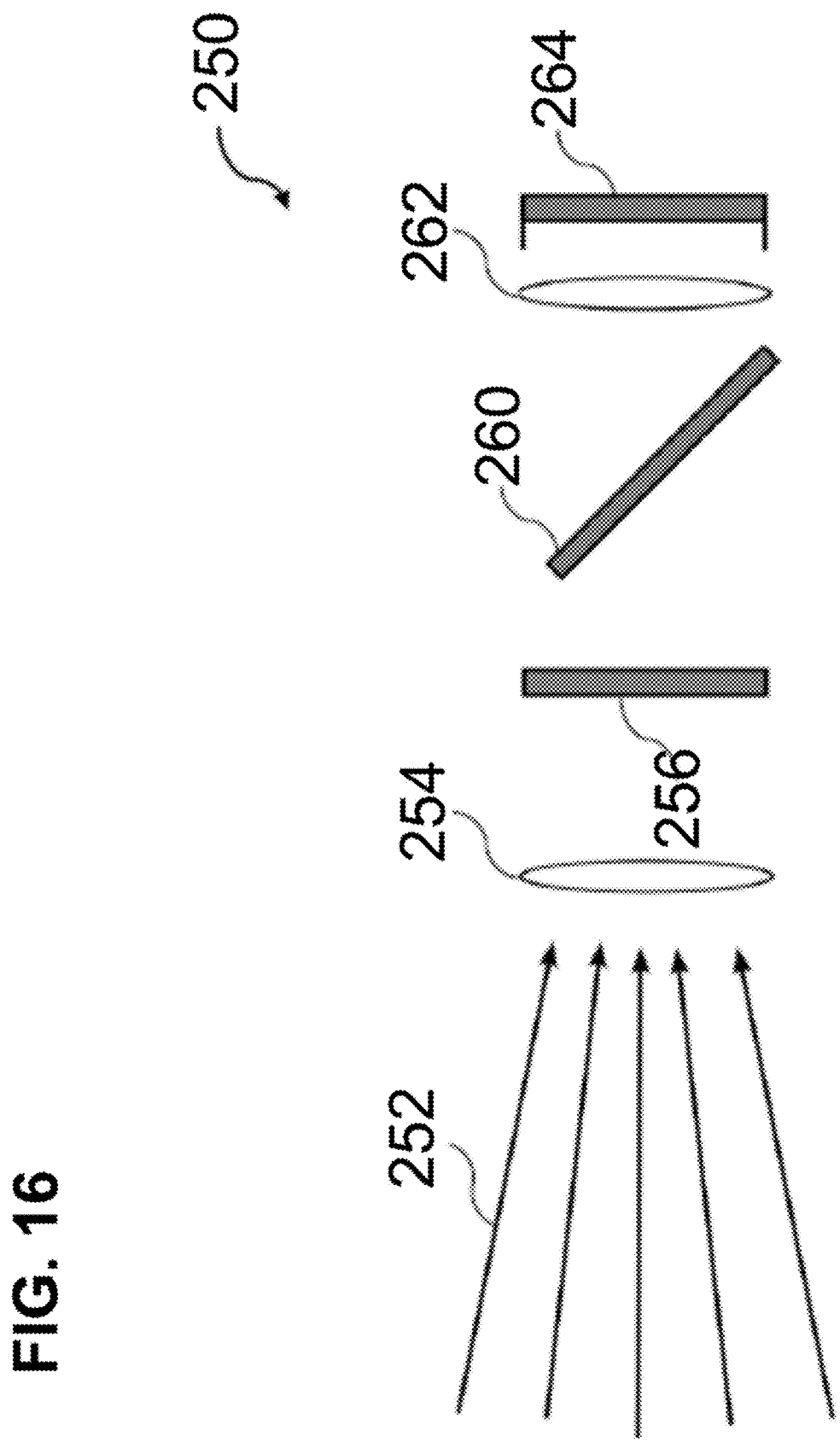
FIG. 16 illustrates an exemplary imaging module of the fluorescence imaging system in FIG. 1, the imaging module comprising a camera module.

Referring back to FIG. 1, in various embodiments, the imaging module 13 may be a component of, for example, the fluorescence imaging system 10 configured to acquire the time series of fluorescence images (e.g., video) from the fluorescence emission from the fluorescence imaging agent 17. Referring to FIG. 16, there is shown an exemplary embodiment of an imaging module 13 comprising a camera module 250. As is shown in FIG. 16, the camera module 250 acquires images of the fluorescence emission 252 from the fluorescence imaging agent 17 in the tissue (e.g., in blood) (not shown) by using a system of imaging optics (e.g., front element 254, rejection filter 256, dichroic 260 and rear element 262) to collect and focus the fluorescence emission onto an image sensor assembly 264 comprising at least one 2D solid state image sensor. A rejection filter 256 may be, for example, a notch filter used to reject a band of wavelengths corresponding to the excitation light. A dichroic 260 may be, for example, a dichroic mirror used to selectively pass one subset of the incoming light wavelength spectrum and redirect remaining wavelengths off of the optical path for rejection or towards a separate image sensor. The solid state image sensor may be a charge coupled device (CCD), a CMOS sensor, a CID or similar 2D sensor technology. The charge that results from the optical signal transduced by the image sensor assembly 264 is converted to an electrical video signal, which includes both digital and analog video signals, by the appropriate read-out and amplification electronics in the camera module 250.

According to some embodiments, excitation wavelength of about 800 nm+/−10 nm and emission wavelengths of >820 nm are used along with NIR compatible optics for ICG fluorescence imaging. A skilled person will appreciate that other excitation and emission wavelengths may be used for other imaging agents.

Referring back to FIG. 1, in various embodiments, the processor assembly 16 comprises, for example,

- a processor module (not shown) configured to perform various processing operations, including executing instructions stored on computer-readable medium, wherein the instructions cause one or more of the systems described herein to execute the methods and techniques described herein, and
- a data storage module (not shown) to record and store the data from the operations, as well as to store, in some embodiments, instructions executable by the processor module to implement the methods and techniques disclosed herein.

In various embodiments, the processor module comprises any computer or computing means such as, for example, a tablet, laptop, desktop, networked computer, or dedicated standalone microprocessor. Inputs are taken, for example, from the image sensor 264 of the camera module 250 shown in FIG. 16, from the solid state photodiode in the light source 200 in FIG. 15, and from any external control hardware such as a footswitch or remote-control. Output is provided to the laser diode driver, and optical alignment aids. In various embodiments, the processor assembly 16 (FIG. 1) may have a data storage module with the capability to save the time series of input data (e.g., image data) to a tangible non-transitory computer readable medium such as, for example, internal memory (e.g. a hard disk or flash memory), so as to enable recording and processing of data. In various embodiments, the processor module may have an internal clock to enable control of the various elements and ensure correct timing of illumination and sensor shutters. In various other embodiments, the processor module may also provide user input and graphical display of outputs. The fluorescence imaging system may optionally be configured with a video display (not shown) to display the images as they are being acquired or played back after recording, or further to visualize the data generated at various stages of the method as was described above.

In operation, and with continuing reference to the exemplary embodiments in FIGS. 1, 15 and 16, the subject is in a position for imaging where the anatomical area of interest of the subject is located beneath both the illumination module 11 and the imaging module 13 such that a substantially uniform field of illumination is produced across substantially the entire area of interest. In various embodiments, prior to the administration of the fluorescence imaging agent 17 to the subject, an image may be acquired of the area of interest for the purposes of background deduction. For example, in order to do this, the operator of the fluorescence imaging system 10 in FIG. 1 may initiate the acquisition of the time series of fluorescence images (e.g., video) by depressing a remote switch or foot-control, or via a keyboard (not shown) connected to the processor assembly 16. As a result, the illumination source 15 is turned on and the processor assembly 16 begins recording the fluorescence image data provided by the image acquisition assembly 13. In lieu of the pulsed mode discussed above, it will be understood that, in some embodiments, the illumination source 15 can comprise an emission source which is continuously on during the image acquisition sequence. When operating in the pulsed mode of the embodiment, the image sensor 264 in the camera module 250 (FIG. 16) is synchronized to collect fluorescence emission following the laser pulse produced by the diode laser 202 in the light source 200 (FIG. 15). In this way, maximum fluorescence emission intensity is recorded, and signal-to-noise ratio is optimized. In this embodiment, the fluorescence imaging agent 17 is administered to the subject and delivered to the area of interest via arterial flow. Acquisition of the time series of fluorescence images is initiated, for example, shortly after administration of the fluorescence imaging agent 17, and the time series of fluorescence images from substantially the entire area of interest are acquired throughout the ingress of the fluorescence imaging agent 17. The fluorescence emission from the region of interest is collected by the collection optics of the camera module 250. Residual ambient and reflected excitation light is attenuated by subsequent optical elements (e.g., optical element 256 in FIG. 16 which may be a filter) in the camera module 250 so that the fluorescence emission can be acquired by the image sensor assembly 264 with minimal interference by light from other sources.

In various embodiments, the processor is in communication with the imaging system or is a component of the imaging system. The program code or other computer-readable instructions, according to the various embodiments, can be written and/or stored in any appropriate programming language and delivered to the processor in various forms, including, for example, but not limited to information permanently stored on non-writeable storage media (e.g., read-only memory devices such as ROMs or CD-ROM disks), information alterably stored on writeable storage media (e.g., hard drives), information conveyed to the processor via transitory mediums (e.g., signals), information conveyed to the processor through communication media, such as a local area network, a public network such as the Internet, or any type of media suitable for storing electronic instruction. In various embodiments, the tangible non-transitory computer readable medium comprises all computer-readable media. In some embodiments, computer-readable instructions for performing one or more of the methods or techniques discussed herein may be stored solely on non-transitory computer readable media.

In some embodiments, the illumination and imaging system may be a component of a medical imaging system such as the fluorescence medical imaging system 10, which acquires medical image data. In embodiments where the illumination and imaging system is a component of the imaging system, such as the fluorescence imaging system described above, the light source, illumination module, imaging module and the processor of the medical imaging system may function as the camera assembly and the processor of the illumination and imaging system. A skilled person will appreciate that imaging systems other than fluorescence imaging systems may be employed for use with illumination and/or imaging systems such as those described herein, depending on the type of imaging being performed.

Example Imaging Agents for Use in Generating Image Data

According to some embodiments, in fluorescence medical imaging applications, the imaging agent is a fluorescence imaging agent such as, for example, indocyanine green (ICG) dye, ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 µM to about 10 µM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. A fluorescence dye includes any non-toxic fluorescence dye. In certain embodiments, the fluorescence dye optimally emits fluorescence in the near-infrared spectrum. In certain embodiments, the fluorescence dye is or comprises a tricarbocyanine dye. In certain embodiments, the fluorescence dye is or comprises indocyanine green (ICG), methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality.

In some embodiments, the fluorescence imaging agent used in combination with the methods and systems described herein may be used for blood flow imaging, tissue perfusion imaging, lymphatic imaging, or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva). In some embodiments, the fluorescence imaging agent may be administered in sufficient concentrations and in a suitable manner so as to effect lymphatic imaging.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through microvasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

By way of summation and review, one or more embodiments may accommodate varied working distances while providing a flat illumination field and matching an illumination field to a target imaging field, thus allowing accurate quantitative imaging applications. An imaging element that focuses light from a target onto a sensor may be moved in synchrony with steering of the illumination field. Additionally or alternatively, a drape may be used that insures a close fit between a drape lens and a window frame of the device. Additionally or alternatively, one or more embodiments may allow ambient light to be subtracted from light to be imaged using a single sensor and controlled timing of illumination and exposure or detection. Additionally or alternatively, one or more embodiments may allow the display of a normalized fluorescence intensity measured within a target reticle region of an image frame.

In contrast, when illumination and imaging devices do not conform illumination to the target imaging field of view or provide a flat, i.e., even or substantially uniform, illumination field, illumination and image quality may suffer. An uneven illumination field can cause distracting and inaccurate imaging artifacts, especially for hand held imaging devices and when used at varied working distances, while excess light outside the imaging field of view reduces device efficiency and can distract the user when positioning the device.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method embodiments described herein.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A processor to image a target, the processor to, within a period:
    turn on an excitation light source to generate an excitation pulse to illuminate the target;
    turn on a white light source to generate a white pulse to illuminate the target such that the white pulse does not overlap the excitation pulse and the white pulse is generated at least twice within the period;
    expose an image sensor for a fluorescent exposure time during the excitation pulse;
    expose the image sensor for a visible exposure time during at least one white pulse;
    detect outputs from the image sensor;
    compensate for ambient light; and
    output a resultant image, wherein, to compensate for ambient light, the processor is to:
- expose a first set of sensor pixel rows of the image sensor for a fraction of the fluorescent exposure time; and
- expose a second set of sensor pixel rows of the image sensor for all of the fluorescent exposure time.

2. The processor as claimed in claim 1, wherein the fraction of the exposure time equals a width of the excitation pulse.

3. The processor as claimed in claim 1, wherein the visible exposure time is for one white pulse within the period.

4. The processor as claimed in claim 1, wherein the visible exposure time is for two white pulses within the period.

5. The processor as claimed in claim 1, wherein, to compensate for ambient light, the processor is to:
- expose the image sensor for a background exposure time when target is not illuminated at least once within the period.

6. A method for imaging a target, within a period, the method comprising:
- generating an excitation pulse to illuminate the target;
- generating a white pulse to illuminate the target such that the white pulse does not overlap the excitation pulse and the white pulse is generated at least twice within the period;
- exposing an image sensor for a fluorescent exposure time during the excitation pulse;
- exposing the image sensor for a visible exposure time during at least one white pulse;
- detecting outputs from the image sensor;
- compensating for ambient light including
  - exposing a first set of sensor pixel rows of the image sensor for a fraction of the fluorescent exposure time; and
  - exposing a second set of sensor pixel rows of the image sensor for all of the fluorescent exposure time; and
- outputting a resultant image.

7. The method as claimed in claim 6, wherein compensating for ambient light includes:
- exposing the image sensor for a background exposure time when target is not illuminated at least once within the period.

8. The method as claimed in claim 6, wherein generating the excitation pulse includes providing uniform, anamorphic illumination to the target.

9. The method as claimed in claim 8, wherein providing uniform, anamorphic illumination to the target includes overlapping illumination from at least two illumination ports.

10. The method as claimed in claim 6, wherein exposing the image sensor for the fluorescent exposure time includes providing a wavelength-dependent aperture upstream of the image sensor during the exposure, the wavelength-dependent aperture to block visible light outside a central region.

11. The method as claimed in claim 9, wherein overlapping illumination from at least two illumination ports includes steering illumination from at least two illumination ports in accordance with a change of working distance.

12. A processor to image a target, the processor to, within a period:
- turn on an excitation light source to generate an excitation pulse to illuminate the target;
- turn on a white light source to generate a white pulse to illuminate the target such that the white pulse does not overlap the excitation pulse and the white pulse is generated at least twice within the period;
- expose an image sensor for a fluorescent exposure time during the excitation pulse;
- expose the image sensor for a visible exposure time during at least one white pulse, wherein a number of visible exposure times is less than a number of white pulses;
- detect outputs from the image sensor;
- compensate for ambient light; and
- output a resultant image.

13. The processor as claimed in claim 12, wherein to generate the excitation pulse, the processor is to provide uniform, anamorphic illumination to the target.

14. The processor as claimed in claim 13, wherein to provide uniform, anamorphic illumination to the target, the processor is to steer illumination from at least two illumination ports in accordance with a change of working distance such that illumination from the at least two illumination ports overlaps at the target.

* * * * *